United States Patent
Singh et al.

(10) Patent No.: US 9,250,243 B2
(45) Date of Patent: *Feb. 2, 2016

(54) DRUG SELECTION FOR LUNG CANCER THERAPY USING ANTIBODY-BASED ARRAYS

(75) Inventors: Sharat Singh, Los Altos Hills, CA (US); Jeanne Harvey, Livermore, CA (US)

(73) Assignee: NESTEC S.A., Vevey (CH)

( * ) Notice: Subject to any disclaimer, the term of this patent is extended or adjusted under 35 U.S.C. 154(b) by 116 days.

This patent is subject to a terminal disclaimer.

(21) Appl. No.: 12/172,100

(22) Filed: Jul. 11, 2008

(65) Prior Publication Data

US 2009/0035792 A1 Feb. 5, 2009
US 2011/0275097 A9 Nov. 10, 2011

Related U.S. Application Data

(63) Continuation-in-part of application No. 12/046,381, filed on Mar. 11, 2008, now Pat. No. 8,658,388, which is a continuation of application No. PCT/US2007/079002, filed on Sep. 20, 2007.

(60) Provisional application No. 60/949,820, filed on Jul. 13, 2007, provisional application No. 60/913,087, filed on Apr. 20, 2007, provisional application No. 61/007,527, filed on Sep. 21, 2006.

(51) Int. Cl.
G01N 33/574 (2006.01)
G01N 33/50 (2006.01)
G01N 33/53 (2006.01)

(52) U.S. Cl.
CPC ...... *G01N 33/57423* (2013.01); *G01N 33/5041* (2013.01); *G01N 33/5044* (2013.01); *G01N 33/5082* (2013.01); *G01N 2500/10* (2013.01); *G01N 2800/52* (2013.01)

(58) Field of Classification Search
CPC ............................... C40B 30/00; C40B 30/04
USPC .......................................................... 509/9
See application file for complete search history.

(56) References Cited

U.S. PATENT DOCUMENTS

| | | | |
|---|---|---|---|
| 4,233,402 A | 11/1980 | Maggio et al. | |
| 4,975,532 A | 12/1990 | Rowley et al. | |
| 5,089,419 A | 2/1992 | Kuniyuki | |
| 5,120,660 A | 6/1992 | Kuniyuki | |
| 5,445,944 A | 8/1995 | Ullman | |
| 5,516,931 A | 5/1996 | Giese et al. | |
| 5,527,684 A | 6/1996 | Mabile et al. | |
| 5,876,944 A | 3/1999 | Kuo | |
| 6,201,109 B1 | 3/2001 | Avnur et al. | |
| 6,335,173 B1 * | 1/2002 | Kaplan | 435/7.2 |
| 6,406,913 B1 | 6/2002 | Ullman et al. | |
| 6,511,809 B2 | 1/2003 | Baez et al. | |
| 6,627,400 B1 | 9/2003 | Singh et al. | |
| 6,649,351 B2 | 11/2003 | Matray et al. | |
| 6,659,351 B1 | 12/2003 | Bailleu et al. | |
| 6,770,439 B2 | 8/2004 | Singh et al. | |
| 6,818,399 B2 | 11/2004 | Singh et al. | |
| 6,949,347 B2 | 9/2005 | Singh et al. | |
| 6,972,198 B2 | 12/2005 | Craig et al. | |
| 7,101,682 B2 | 9/2006 | Ullman et al. | |
| 7,279,286 B2 | 10/2007 | Kannt et al. | |
| 7,402,399 B2 | 7/2008 | Mukherjeei et al. | |
| 7,537,938 B2 | 5/2009 | Kirakossian et al. | |
| 7,695,924 B2 | 4/2010 | Perez et al. | |
| 7,695,926 B2 | 4/2010 | Perez et al. | |
| 8,163,499 B2 | 4/2012 | Singh et al. | |
| 8,609,349 B2 | 12/2013 | Singh et al. | |
| 2002/0142361 A1 | 10/2002 | Emmert-Buck | |
| 2002/0168641 A1 | 11/2002 | Mortensen et al. | |
| 2003/0059811 A1 | 3/2003 | Djaballah et al. | |
| 2003/0087311 A1 | 5/2003 | Wolf | |
| 2003/0153013 A1 | 8/2003 | Huang | |
| 2003/0153014 A1 | 8/2003 | Shen et al. | |
| 2003/0190689 A1 | 10/2003 | Crosby et al. | |
| 2004/0077090 A1 | 4/2004 | Short | |
| 2004/0106161 A1 | 6/2004 | Bossenmaier et al. | |
| 2004/0157271 A1 | 8/2004 | Kirakossian et al. | |
| 2004/0175696 A1 | 9/2004 | Ullman et al. | |
| 2004/0235002 A1 | 11/2004 | Holmes et al. | |
| 2004/0265923 A1 * | 12/2004 | Gilmore et al. | 435/7.9 |
| 2004/0265938 A1 | 12/2004 | Remacle et al. | |
| 2005/0069962 A1 * | 3/2005 | Archer et al. | 435/7.9 |
| 2005/0153342 A1 | 7/2005 | Chen | |
| 2006/0024723 A1 | 2/2006 | Hussa et al. | |
| 2006/0024846 A1 | 2/2006 | Singh et al. | |
| 2006/0127945 A1 | 6/2006 | Preaudat et al. | |
| 2007/0111944 A1 | 5/2007 | Scrofani et al. | |
| 2007/0269902 A1 | 11/2007 | Beechem et al. | |
| 2008/0096235 A1 | 4/2008 | Kimberly et al. | |
| 2008/0176229 A1 | 7/2008 | Agus et al. | |
| 2008/0187948 A1 | 8/2008 | Chan-Hui et al. | |

(Continued)

FOREIGN PATENT DOCUMENTS

CA 2 588 992 A1 6/2006
EP 0 310 132 A2 4/1989

(Continued)

OTHER PUBLICATIONS

Dorland's Medical Dictionary for Healthcare Consumers (non-small cell carcinoma, 2007, Merck, Sharp & Dohme Corp.).*

(Continued)

*Primary Examiner* — Peter J Reddig
(74) *Attorney, Agent, or Firm* — Kilpatrick Townsend & Stockton LLP

(57) ABSTRACT

The present invention provides compositions and methods for detecting the activation states of components of signal transduction pathways in tumor cells. Information on the activation states of components of signal transduction pathways derived from use of the invention can be used for cancer diagnosis, prognosis, and in the design of cancer treatments.

48 Claims, 5 Drawing Sheets

(56) References Cited

U.S. PATENT DOCUMENTS

| | | | |
|---|---|---|---|
| 2008/0261829 | A1 | 10/2008 | Harvey et al. |
| 2009/0035792 | A1 | 2/2009 | Singh et al. |
| 2009/0124511 | A1 | 5/2009 | Archer et al. |
| 2010/0021457 | A1 | 1/2010 | Pfleger et al. |
| 2010/0167945 | A1 | 7/2010 | Singh et al. |
| 2011/0275097 | A9 | 11/2011 | Singh et al. |
| 2011/0281748 | A1 | 11/2011 | Singh et al. |
| 2012/0231965 | A1 | 9/2012 | Kim et al. |
| 2012/0270745 | A1 | 10/2012 | Singh et al. |
| 2013/0045880 | A1 | 2/2013 | Singh et al. |
| 2013/0324430 | A1 | 12/2013 | Kim et al. |
| 2014/0187445 | A1 | 7/2014 | Harvey et al. |
| 2014/0349865 | A1 | 11/2014 | Singh et al. |
| 2015/0051107 | A1 | 2/2015 | Harvey et al. |

FOREIGN PATENT DOCUMENTS

| | | | |
|---|---|---|---|
| EP | 1 145 004 B1 | 4/2004 | |
| EP | 1 673 635 B1 | 4/2009 | |
| EP | 2065475 A1 | 6/2009 | |
| JP | H06-109734 A | 4/1994 | |
| JP | 07-216000 A2 | 8/1995 | |
| JP | H10-501070 A | 1/1998 | |
| JP | 2002-214237 A | 7/2002 | |
| JP | 2002-530629 | 9/2002 | |
| JP | 2005-500045 A | 1/2005 | |
| JP | 2007-510910 A | 4/2007 | |
| JP | 2008-292424 A | 12/2008 | |
| RU | 2149404 C1 | 5/2000 | |
| RU | 2165081 C | 4/2001 | |
| WO | WO 96/07103 A1 | 3/1996 | |
| WO | WO 00/29609 | 5/2000 | |
| WO | WO 01/27611 A2 | 4/2001 | |
| WO | WO 02/090964 A | 11/2002 | |
| WO | WO 03/006104 A2 | 1/2003 | |
| WO | WO 03/087761 A2 | 10/2003 | |
| WO | WO 2004/071572 A2 | 8/2004 | |
| WO | WO 2005/044794 A2 | 5/2005 | |
| WO | WO 2005/095965 A1 | 10/2005 | |
| WO | WO 2006/031815 A1 * | 3/2006 | ............... C12Q 1/68 |
| WO | WO 2006/044748 A2 | 4/2006 | |
| WO | WO 2006/045991 A1 | 5/2006 | |
| WO | WO 2006/054991 A | 5/2006 | |
| WO | WO 2006/055739 A2 | 5/2006 | |
| WO | WO 2006/105642 A1 | 10/2006 | |
| WO | WO 2006/119980 A1 | 11/2006 | |
| WO | WO 2007/130677 A2 | 11/2007 | |
| WO | WO 2008/019375 A2 | 2/2008 | |
| WO | WO 2008/036802 A | 3/2008 | |
| WO | WO 2008/064884 A1 | 6/2008 | |
| WO | WO 2009/012140 A2 | 1/2009 | |
| WO | WO 2009/108637 A1 | 9/2009 | |
| WO | WO 2011/008990 A1 | 1/2011 | |

OTHER PUBLICATIONS

Humblet, Y. (Expert Opin. Pharamcother. 2004 5(7): 1621-1633).*
Langer, CJ (Int. J. Radiation Oncology Biol. Phys. 2004 58(3): 991-1002).*
Glucose Oxidase (MeSH http://www.ncbi.nlm.nih.gov/mesh/?term=glucose+oxidase, 1964), "MeSH".*
Langry et al., U.S. Dept. of Energy Report No. UCRL-ID-136797, Nov. 5, 1999, 30 pages.
Gembitsky, Dmitry et al. "A Prototype Antibody Microarray Platform to Monitor Changes in Protein Tyrosine Phosphorylation," Molecular & Cellular Proteomics, 2004, vol. 3, No. 11, pp. 1102-1118.
Haab, Brian "Antibody Arrays in Cancer Research," Molecular & Cellular Proteomics, 2005, vol. 4, No. 4, pp. 377-383.
Haab, Brian "Applications of Antibody array platforms," Current Opinion in Biotechnology, 2006, vol. 17, pp. 415-421.
Kopf, Eliezer et al., "Antibody arrays—An emerging tool in cancer proteomics," The International Journal of Biochemistry & Cell Biology, 2007, vol. 39, pp. 1305-1317.

Angenendt et al. "3D Protein Microarrays: Performing Multiplex Immunoassays on a Single Chip," Anal. Chem., 2003, vol. 75, pp. 4368-4372.
Blume-Jensen et al. "Oncogenic kinase signalling," Nature, 2001, vol. 411, pp. 355-365.
Gembitsky et al. "A Prototype Antibody Microarray Platform to Monitor Changes in Protein Tyrosine Phosphorylation," Molecular & Cellular Proteomics, 2004, vol. 3, No. 11, pp. 1102-1118.
Hudelist et al. "Use of high-throughput protein array for profiling of differentially expressed proteins in normal and malignant breast tissue," Breast Cancer Research and Treatment, 2004, vol. 86, pp. 281-291.
Kopf et al., "Antibody arrays—An emerging tool in cancer proteomics," The International Journal of Biochemistry & Cell Biology, 2007, vol. 39, pp. 1305-1317.
Nielsen et al., "Profiling receptor tyrosine kinase activation by using Ab microarrays." PNAS, vol. 100, No. 16, pp. 9330-9335, Aug. 5, 2003.
Nielsen et al., "Multiplexed sandwich assays in microarray format." J. Immunological Methods, vol. 290, No. 1-2, pp. 107-120, Jul. 2004.
Bartling et al. "Comparative application of antibody and gene array for expression profiling in human squamous cell lung carcinoma," Lung Cancer, 2005, vol. 49, No. 2, pp. 145-154.
Restriction Requirement mailed on Jun. 25, 2010 in U.S. Appl. No. 12/046,381, filed Mar. 11, 2008, 12 pages.
Scaltriti, M. et al., "Expression of p95HER2, a truncated form of the HER2 receptor and response to anti-HER2 therapies in breast cancer," JNCI, 2007, 99(8):628-638.
Yonemura, Y. et al., "Role of vascular endothelial growth factor C expression in the development of lymph node metastasis in gastric cancer," Clinical Cancer Research, 1999, 5:1823-1829.
Arpino et al., "Infiltrating lobular carcinoma of the breast: tumor characteristics and clinical outcome," Breast Cancer Research, 2003, vol. 6, pp. R149-R156.
Lu et al., "Construction of an antibody microarray based on agarose-coated slides," Electrophoesis, 2007, vol. 28, pp. 406-413.
Mouridsen et al., "Phase III of Letrozole Versus Tamoxifen as First-Line Therapy of Advanced Breast Cancer in Postmenopausal Women: Analysis of Survival and Update of Efficacy from the International Letrozole Breast Cancer Group," Journal of Clincal Oncology, 2003, vol. 21, pp. 2101-2109.
Pearce et al., "Modulation of Estrogen Receptor α Function and Stability by Tamoxifen and a Critical Amino Acid (Asp-538) in Helix 12," Journal of Biological Chemistry, 2003, vol. 278, No. 9, pp. 7630-7638.
Sanchez-Carbayo, "Antibody Arrays: Technical Considerations and Clinical Applications in Cancer," Clinical Chemistry, 2006, vol. 52, pp. 1651-1659.
Bachleitner-Hofmann, T. et al., "HER kinase activation confers resistance to MET tyrosine kinase inhibition in MET oncogene-addicted gastric cancer cells," Mol. Cancer Ther., 7:3499-3508, 2008.
Engelman, J. et al., "ErbB-3 mediates phosphoinositide 3-kinase activity in gefitinib-sensitive non-small cell lung cancer cell lines," PNAS, 2005, 102(10):3788-93.
Engelman, J. et al., "Met amplification leads to gefitinib resistance in lung cancer by activating ERBB3 signaling," Science, 316(5827):1039-1043, 2007.
Huang, F. et al., "The mechanisms of differential sensitivity to an insulin-like growth factor-1 receptor inhibitor (BMS-536924) and rationale for combining with EGFR/HER2 inhibitors," Cancer Res., 69(1):161-170, 2009.
Kelkar, S. et al., "Cytoplasmic Dynein Mediates Adenovirus Binding to Microtubules," J. Virol., 2004, 78(18):10122-10132.
Kuhlmann, W.D. et al., "Glucose oxidase as label in histological immunoassays with enzyme-amplification in a two-step technique: coimmobilized horseradish peroxidase as secondary system enzyme for chromogen oxidation," Histochemistry, 85:13-17, 1986.
Samuilov, V.D., Immunofermentnyi analiz [Immunoenzyme analysis], Sorosovskii obrazovatelnyi zhurnal, No. 12, pp. 9-15, 1999.
Zhou, B. et al., "Targeting ADAM-mediated ligand cleavage to inhibit HER3 and EGFR pathways in non-small cell lung cancer," Cancer Cell, 2006, 10:39-50.

(56) References Cited

OTHER PUBLICATIONS

Daly et al., "Evaluating concentration estimation errors in ELISA microarray experiments," BMC Bioinformatics, 2005, 6:17, printed as pp. 1/11 to 11/11.

Becker et al., "Role of receptor tyrosine kinases in gastric cancer: new targets for a selective therapy," World J of Gasteroenterol, vol. 12, No. 21, pp. 3297-3305, Jun. 7, 2006.

Litt et al., Chapter 10, "Tyramide signal amplification: Applications in detecting infectious agents," in Rapid Detection of Infectious Agents, Ed. Specter et al., Plenum Press, New York, 1998, pp. 159-173.

Stern, D., "Phosphoproteornics for Oncology discovery and treatment," Expert Opinion on Therapeutic Targets, vol. 9, No. 4, pp. 851-860, Aug. 2005.

Wiese et al., "Simultaneous multianylyte ELISA performed on a microarray platform," Clinical Chemistry, vol. 47, No. 8, pp. 1450-1457, 2001.

Woodbury et al., "Elevated HGF levels in sera from, breast cancer patients detected using a protein microarray ELISA," Journal of Proteome Research, vol. 1, pp. 233-237, 2002.

Yan, Jing et al., "Role of antibody chip in analysis of inflammatory cytokine expression in severe sepsis," *Chin. J. Emerg. Med.*, Sep. 30, 2006, 15(9):830-833.

Ahn et al., "Molecular Markers for Individualized Therapy in Colorectal Cancer: Progress Towards a Pharmacogenomics Array," Curr Pharma and Personalized Medicine, 7:70-80, 2009.

Fiore et al., "Clinical relevance of KRAS mutation detection in metastatic colorectal cancer treated by Cetuximab plus chemotherapy," British J Cancer, 96:1166-69, 2007.

Kim et al., "Highly sensitive proximity mediated immunoassay reveals HER2 status conversion in the circulating tumor cells of metastatic breast cancer patients," Proteome Science, 9:75, 15 pgs., 2011.

Sathyanarayanan et al., "229 Anti-IGF1R therapy with dalotuzumab is efficacious in a sub-set of KRAS mutant cetuximab refractory CRC models," Eur J Cancer, Suppl., 8(7):75, 2010.

Siena et al., "Biomarkers predicting clinical outcome of epidermal growth factor receptor-targeted therapy in metastatic colorectal cancer," J Natl Cancer Inst, 101(19):1308-1324, 2009.

Ubersax et al., "Mechanisms of specificity in protein phosphorylation," Nature, 8:530-541, 2007.

Yasui, W. et al., "Expression of epidermal growth factor receptor in human gastric and colonic carcinomas," Cancer Res, Jan. 1, 1988, 48(1), 137-141.

\* cited by examiner

A. Patient 2002 with 2 CTCs

B. Patient 2015 with 11 CTCs

DRUG SELECTION FOR LUNG CANCER THERAPY USING ANTIBODY-BASED ARRAYS

CROSS-REFERENCE TO RELATED APPLICATIONS

This application claims priority to U.S. Provisional Patent Application No. 60/949,820, filed Jul. 13, 2007, the disclosure of which is hereby incorporated by reference in its entirety for all proposes. This application is also a continuation-in-part of U.S. patent application Ser. No. 12/046,381, filed Mar. 11, 2008, issued as U.S. Pat. No. 8,658,388 which application is a continuation of International Patent Application No. PCT/US07/079002, filed Sep. 20, 2007, which application claims priority to U.S. Provisional Patent Application No. 60/913,087, filed Apr. 20, 2007, and U.S. Provisional Patent Application No. 61/007,527, filed Sep. 21, 2006.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

The process of signal transduction in cells is responsible for a variety of biological functions including cell division and death, metabolism, immune cell activation, neurotransmission, and sensory perception to name but a few. Accordingly, derangements in normal signal transduction in cells can lead to a number of disease states such as diabetes, heart disease, autoimmunity, and cancer.

One well characterized signal transduction pathway is the MAP kinase pathway, which is responsible for transducing the signal from epidermal growth factor (EGF) to the promotion of cell proliferation in cells (see, FIG. 1). EGF binds to a transmembrane receptor-linked tyrosine kinase, the epidermal growth factor receptor (EGFR), which is activated by the binding of EGF. The binding of EGF to EGFR activates the tyrosine kinase activity of the cytoplasmic domain of the receptor. One consequence of this kinase activation is the autophosphorylation of EGFR on tyrosine residues. The phosphorylated tyrosine residues on the activated EGFR provide a docking site for the binding of SH2 domain containing adaptor proteins such as GRB2. In its function as an adaptor, GRB2 further binds to a guanine nucleotide exchange factor, SOS, by way of an SH3 domain on GRB2. The formation of the complex of EGFR-GRB2-SOS leads to SOS activation to a guanine nucleotide exchange factor that promotes the removal of GDP from Ras. Upon removal of GDP, Ras binds GTP and becomes activated.

Following activation, Ras binds to and activates the protein kinase activity of RAF kinase, a serine/threonine-specific protein kinase. What follows is the activation of a protein kinase cascade that leads to cell proliferation. In outline, RAF kinase then phosphorylates and activates MEK, another serine/threonine kinase. Activated MEK phosphorylates and activates mitogen-activated protein kinase (MAPK). Among the targets for further phosphorylation by MAPK are 40S ribosomal protein S6 kinase (RSK). The phosphorylation of RSK by MAPK results in activation of RSK, which in turn phosphorylates ribosomal protein S6. Another known target of MAPK is the proto-oncogene, c-Myc, a gene important for cell proliferation, which is mutated in a variety of cancers. MAPK also phosphorylates and activates another protein kinase, MNK, which in turn phosphorylates the transcription factor, CREB. Indirectly, MAPK also regulates the transcription of the Fos gene, which encodes yet another transcription factor involved in cell proliferation. By altering the levels and activities of such transcription factors, MAPK transduces the original extracellular signal from EGF into altered transcription of genes that are important for cell cycle progression.

Given the central role that signal transduction pathways play in cell growth, it is not surprising that many cancers arise as a result of mutations and other alterations in signal transduction components that result in aberrant activation of cell proliferation pathways. For example, overexpression or hyperactivity of EGFR has been associated with a number of cancers, including glioblastoma multiforme, colon cancer, and lung cancer. This has prompted the development of anticancer therapeutics directed against EGFR, including gefitinib and erlotinib for lung cancer, and cetuximab for colon cancer.

Cetuximab is an example of a monoclonal antibody inhibitor, which binds to the extracellular ligand binding domain of EGFR, thus preventing the binding of ligands which activate the EGFR tyrosine kinase. In contrast, gefitinib and erlotinib are small molecules which inhibit the intracellularly-located EGFR tyrosine kinase. In the absence of kinase activity, EGFR is unable to undergo autophosphorylation at tyrosine residues, which is a prerequisite for binding of downstream adaptor proteins, such as GRB2. By halting the signaling cascade in cells that rely on this pathway for growth, tumor proliferation and migration is diminished.

Additionally, other studies have shown that about 70% of human melanomas and a smaller fraction of other tumors have a point mutation (V599E) in the Raf gene which leads to persistent activation of the MAPK pathway (see, e.g., Davies et al., Nature, 417:949-954 (2002)). Such results suggest that mutations in particular signal transduction pathways may be characteristic of particular types of tumors and that such specific, altered signal transduction pathways may be a promising target for chemotherapeutic intervention.

Given that different cancer treatments, particularly cancer chemotherapy, may function either directly or indirectly by means of either blocking or activating cellular signal transduction pathways that are involved in cell proliferation or death, respectively, the activity of a given signal transduction pathway in a particular form of cancer may serve as a good indicator of the efficacy of various cancer treatments. Accordingly, in addition to fulfilling other needs, the present invention provides a method for evaluating the effectiveness of potential anticancer therapies for an individual patient. As such, the present invention provides methods for assisting a physician in selecting a suitable cancer therapy at the right dose and at the right time for every patient.

BRIEF SUMMARY OF THE INVENTION

The present invention provides compositions and methods for detecting the activation states of components of signal transduction pathways in tumor cells (e.g., circulating cells of a lung tumor). Information on the activation states of components of signal transduction pathways derived from use of the invention can be used for cancer diagnosis, prognosis, and in the design of cancer treatments.

In one aspect, the present invention provides a method for selecting a suitable anticancer drug for the treatment of a lung tumor, the method comprising:
(a) isolating cells of the lung tumor after administration of an anticancer drug, or prior to incubation with the anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) determining whether the anticancer drug is suitable or unsuitable for the treatment of the lung tumor by comparing the activation state detected for the one or more analytes with a reference activation profile generated in the absence of the anticancer drug.

In another aspect, the present invention provides a method for selecting a subject having a lung tumor who is a suitable candidate for treatment with an anticancer drug, the method comprising:
(a) isolating cells of the lung tumor after administration of an anticancer drug, or prior to incubation with the anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) determining whether the subject is suitable or unsuitable for the treatment of the lung tumor by the anticancer drug by comparing the activation state detected for the one or more analytes with a reference activation profile generated in the absence of the anticancer drug.

In another aspect, the present invention provides a method for identifying the response of a lung tumor to treatment with an anticancer drug, the method comprising:
(a) isolating cells of the lung tumor after administration of the anticancer drug, or prior to incubation with the anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) identifying the lung tumor as responsive or non-responsive to treatment with the anticancer drug by comparing the activation state detected for the one or more analytes with a reference activation profile generated in the absence of the anticancer drug.

In yet another aspect, the present invention provides a method for predicting the response of a subject having a lung tumor to treatment with an anticancer drug, the method comprising:
(a) isolating cells of the lung tumor after administration of the anticancer drug, or prior to incubation with the anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) predicting the likelihood that the subject will respond to treatment with the anticancer drug by comparing the activation state detected for the one or more analytes with a reference activation profile generated in the absence of the anticancer drug.

In yet another aspect, the present invention provides a method for prognosing clinical outcome for a subject having a lung tumor treated with an anticancer drug, the method comprising:
(a) isolating cells of the lung tumor after administration of an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) prognosing the clinical outcome for the subject treated with the anticancer drug by comparing the activation state detected for the one or more analytes with a reference activation profile generated in the absence of the anticancer drug.

In a further aspect, the present invention provides an array having superior dynamic range comprising a plurality of dilution series of capture antibodies restrained on a solid support, wherein the capture antibodies in each dilution series are specific for one or more analytes corresponding to a component of a signal transduction pathway in a cellular extract.

Other objects, features, and advantages of the present invention will be apparent to one of skill in the art from the following detailed description and figures.

DETAILED DESCRIPTION OF THE INVENTION

I. Introduction

Figure 1:
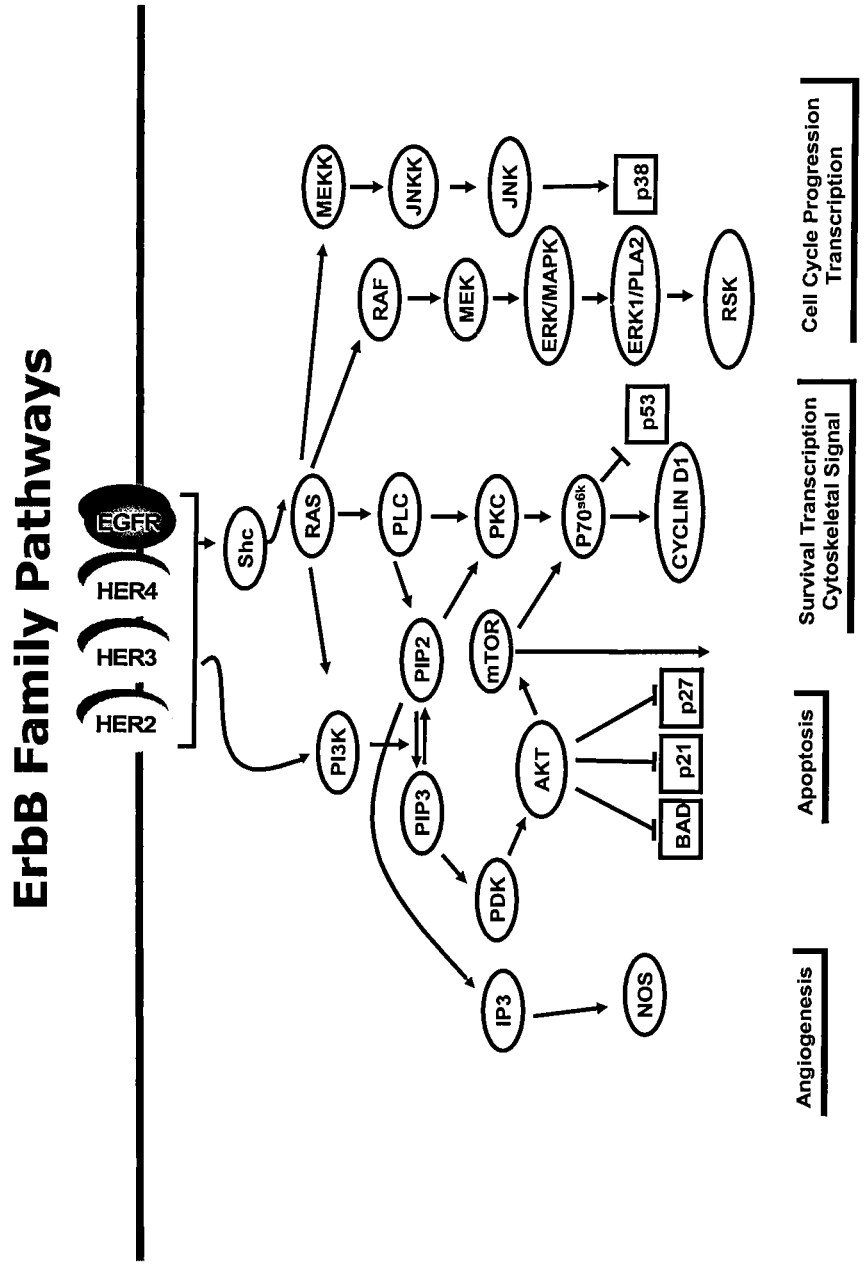
FIG. 1 shows an example of a signal transduction pathway involved in cell proliferation that may be used in the practice of the invention. Depicted are components of the EGFR/MAPK/ERK pathway that is used by cells to convert a mitogenic signal into cell proliferation.

As described above, the activation of signal transduction pathways that are involved in cell proliferation and the deactivation of pathways that are involved in cell death are non-limiting examples of molecular features that characterize many different types of cancer. In many cases, the activity of particular signal transduction pathways, and components thereof, can serve as molecular signatures for a given type of cancer. Such activated components can further provide useful targets for therapeutic intervention. Accordingly, knowledge of the activity level of a particular signal transduction system within a cancer cell prior to, during, and after treatment provides a physician with highly relevant information that can be used to select an appropriate course of treatment to adopt. Furthermore, the continued monitoring of signal transduction pathways that are active in cancer cells as treatment progresses can provide the physician with additional information on the efficacy of treatment, prompting the physician to either continue a particular course of treatment or to switch to another line of treatment, when, for example, cancer cells have become resistant to treatment through further abberations that activate either the same or another signal transduction pathway.

Accordingly, the present invention provides methods and compositions for detecting the expression and activation states of a plurality of deregulated signal transduction molecules in tumor tissue or extratumoral cells such as rare circulating cells of a solid tumor in a specific, multiplex, high-throughput assay. The invention also provides methods and compositions for the selection of appropriate therapy (single drugs or combinations of drugs) to down-regulate or shut down a deregulated signaling pathway. Thus, the invention may be used to facilitate the design of personalized therapies for cancer patients.

The ability to detect and identify tumor cells in the circulation through the determination of the activity of signal transduction pathways at the level of single cells is an important advantage of the present invention. Tumor cells are often found in the blood of patients with various early stages of cancer as "micrometastases" (disseminated tumor cells) and are also found in metastatic cancers. The number of tumor cells in blood will depend on the stage and type of tumor. While biopsies are typically obtained on primary tumors, most metastatic tumors are not biopsied, making molecular analysis of such tumor samples very difficult. During tumor metastasis, the most aggressive tumor cells leave the primary tumor and travel through the blood and lymphatic system to reach a distant location. Thus, circulating tumor cells from blood represent the most aggressive and homogenous population of tumor cells. However, the number of metastatic tumor cells in blood is frequently very low, varying from one to several thousand cells per milliliter of blood. The ability to isolate and assay signal transduction pathways in such rare cells and to apply this information toward more effective cancer treatments is one object of the present invention.

In some embodiments, the multiplex, high-throughput immunoassays of the present invention can detect the activation state of one or more signal transduction molecules in circulating cells of a solid tumor at the single cell level. In fact, signal transduction molecules such as EGFR can be detected with a sensitivity of about 100 zeptomoles and a linear dynamic range of from about 100 zeptomoles to about 100 femtomoles. As such, single-cell detection of the activation state of multiple signal transducers in rare circulating cells facilitates cancer prognosis and diagnosis as well as the design of personalized, targeted therapies.

Rare circulating cells include circulating cells of a solid tumor that have either metastasized or micrometastasized from a solid tumor. Circulating tumor cells, cancer stem cells, and cells that are migrating to a tumor (e.g., due to chemoattraction) such as circulating endothelial progenitor cells, circulating endothelial cells, circulating pro-angiogenic myeloid cells, and circulating dendritic cells are some examples of circulating cells associated with a solid tumor.

Signal transduction molecules of interest are typically extracted shortly after the circulating cells are isolated to preserve their in situ activation state, preferably within about 24, 6, or 1 hr, and more preferably within about 30, 15, or 5 minutes. The isolated cells may also be incubated with one or more growth factors, usually at nanomolar to micromolar concentrations, for about 1-30 minutes to resuscitate or stimulate activation of the signal transduction molecules (see, e.g., Irish et al., Cell, 118:217-228 (2004)).

As explained in greater detail herein, to evaluate potential anticancer therapies for an individual patient, the isolated cells can be incubated with one or more anticancer drugs at varying doses. Growth factor stimulation can then be performed for a few a period of time (e.g., about 1-5 minutes) or for several hours (e.g., about 1-6 hours). The differential activation of signaling pathways with and without anticancer drugs can aid in the selection of a suitable cancer therapy at the proper dose for each individual patient. Circulating cells can also be isolated from a patient sample during anticancer drug treatment and stimulated with one or more growth factors to determine whether a change in therapy should be implemented. As such, the methods of the present invention advantageously assist the clinician in providing the right anticancer drug at the right dose at the right time for every patient.

II. Definitions

As used herein, the following terms have the meanings ascribed to them unless specified otherwise.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; breast cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells. In a preferred embodiment, the lung tumor is derived from a subject with a non-small cell lung cancer such as, for example, a squamous cell carcinoma, an adenocarcinoma, a large cell carcinoma, bronchoalveolar carcinoma (BAC), or oat cell carcinoma.

The term "analyte" includes any molecule of interest, typically a macromolecule such as a polypeptide, whose presence, amount, and/or identity is determined. In certain instances, the analyte is a cellular component of circulating cells of a solid tumor, preferably a signal transduction molecule.

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, and the like.

The term "superior dynamic range" refers to the ability of an assay to detect a specific analyte in as few as one cell or in as many as thousands of cells. For example, the immunoassays described herein possess superior dynamic range because they advantageously detect a particular signal transduction molecule of interest in about 1-10,000 cells using a dilution series of capture antibody concentrations.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR-1/FLT-1, VEGFR-2/FLK-1/KDR, VEGFR-3/FLT-4, FLT-3/FLK-2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, MET, RON, EPHA 1-8, EPHB 1-6, AXL, MER, TYRO3, TIE 1-2, TEK, RYK, DDR 1-2, RET, c-ROS, LTK (leukocyte tyrosine kinase), ALK (anaplastic lymphoma kinase), ROR 1-2, MUSK, AATYK 1-3, and RTK 106; non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as Akt, MAPK/ERK, MEK, RAF, PLA2, MEKK, JNKK, JNK, p38, Shc (p66), PI3K, Ras (e.g., K-Ras, N-Ras, H-Ras), Rho, Rac1, Cdc42, PLC, PKC, p70 S6 kinase, p53, cyclin D1, STAT1, STAT3, PIP2, PIP3, PDK, mTOR, BAD, p21, p27, ROCK, IP3, TSP-1, NOS, PTEN, RSK 1-3, JNK, c-Jun, Rb, CREB, Ki67, and paxillin; and combinations thereof.

As used herein, the term "circulating cells" comprises extratumoral cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.).

The term "sample" as used herein includes any biological specimen obtained from a patient. Samples include, without limitation, whole blood, plasma, serum, red blood cells, white blood cells (e.g., peripheral blood mononuclear cells), saliva, urine, stool (i.e., feces), sputum, bronchial lavage fluid, tears, nipple aspirate, lymph (e.g., disseminated tumor cells of the lymph node), fine needle aspirate, any other bodily fluid, a tissue sample (e.g., tumor tissue) such as a biopsy of a tumor (e.g., needle biopsy), and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the lung, colon, or rectum.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V.

The term "subject" or "patient" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). The arrays used in the assays of the present invention typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample. In preferred embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, Akt, MAPK/ERK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. Non-limiting examples of activation states (listed in parentheses) that are suitable for detection with activation state-dependent antibodies include: EGFR (EGFRvIII, phosphorylated (p-) EGFR, EGFR:Shc, ubiquitinated (u-) EGFR, p-EGFRvIII); ErbB2 (p85:truncated (Tr)-ErbB2, p-ErbB2, p85:Tr-p-ErbB2, Her2:Shc, ErbB2:PI3K, ErbB2:EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); IGF-1R (p-IGF-1R, IGF-1R:IRS, IRS:PI3K, p-IRS, IGF-1R:PI3K); INSR (p-INSR); KIT (p-KIT); FLT3 (p-FLT3); HGFRI (p-HGFRI); HGFR2 (p-HGFR2); RET (p-RET); PDGFRa (p-PDGFRa); PDGFRP (p-PDGFRP); VEGFRI (p-VEGFRI, VEGFRI:PLCg, VEGFR1:Src); VEGFR2 (p-VEGFR2, VEGFR2:PLCy, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); Tie1 (p-Tie1); Tie2 (p-Tie2); EphA (p-EphA); EphB (p-EphB); NFKB and/or IKB (p-IK (S32), p-NFKB (S536), p-P65:IKBa); Akt (p-Akt (T308, S473)); PTEN (p-PTEN); Bad (p-Bad (S112, S136), Bad:14-3-3); mTor (p-mTor (S2448)); p70S6K (p-p70S6K (T229, T389)); Mek (p-Mek (S217, S221)); Erk (p-Erk (T202, Y204)); Rsk-1 (p-Rsk-1 (T357, S363)); Jnk (p-Jnk (T183, Y185)); P38 (p-P38 (T180, Y182)); Stat3 (p-Stat-3 (Y705, S727)); Fak (p-Fak (Y576)); Rb (p-Rb (S249, T252, S780)); Ki67; p53 (p-p53 (S392, S20)); CREB (p-CREB (S133)); c-Jun (p-c-Jun (S63)); cSrc (p-cSrc (Y416)); and paxillin (p-paxillin (Y118)).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "oligonucleotide" refers to a single-stranded oligomer or polymer of RNA, DNA, RNA/DNA hybrid, and/or a mimetic thereof. In certain instances, oligonucleotides are composed of naturally-occurring (i.e., unmodified) nucleobases, sugars, and internucleoside (backbone) linkages. In certain other instances, oligonucleotides comprise modified nucleobases, sugars, and/or internucleoside linkages.

As used herein, the term "mismatch motif" or "mismatch region" refers to a portion of an oligonucleotide that does not have 100% complementarity to its complementary sequence. An oligonucleotide may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "stringent hybridization conditions" refers to conditions under which an oligonucleotide will hybridize to its complementary sequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region) when compared and aligned for maximum correspondence over a comparison window or designated region as measured using a sequence comparison algorithm or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

III. Description of the Embodiments

In one embodiment, the present invention provides methods for detecting the expression and activation states of a plurality of deregulated signal transducers in tumor cells derived from tumor tissue or circulating cells of a solid tumor in a specific, multiplex, high-throughput assay. The invention also provides methods and compositions for the selection of appropriate therapies to down-regulate or shut down one or more deregulated signaling pathways. Thus, embodiments of the invention may be used to facilitate the design of personalized therapies based on the particular molecular signature provided by the collection of activated signal transduction proteins in a given patient's tumor.

Circulating cells of a solid tumor include cells that have either metastasized or micrometastasized from a solid tumor, including cancer stem cells or cells that are migrating to the tumor (e.g., due to chemoattraction), such as endothelial progenitor cells, circulating endothelial cells, pericytes, circulating pro-angiogenic myeloid cells, dendritic cells, etc. Patient samples containing the circulating cells can be obtained from any accessible biological fluid (e.g., whole blood, serum, plasma, sputum, bronchial lavage fluid, urine, nipple aspirate, lymph, saliva, fine needle aspirate, etc.). In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), disseminated tumor cells of the lymph node, and combinations thereof. The plasma or serum fraction usually contains, inter alia, nucleic acids (e.g., DNA, RNA) and proteins that are released by circulating cells of a solid tumor.

The circulating cells are typically isolated from a patient sample using one or more separation methods including, for example, immunomagnetic separation (see, e.g., Racila et al., *Proc. Natl. Acad. Sci. USA,* 95:4589-4594 (1998); Bilkenroth et al., *Int. J. Cancer,* 92:577-582 (2001)), the CellTrack™ System by Immunicon (Huntingdon Valley, Pa.), microfluidic separation (see, e.g., Mohamed et al., *IEEE Trans. Nanobiosci.,* 3:251-256 (2004); Lin et al., Abstract No. 5147, 97th AACR Annual Meeting, Washington, D.C. (2006)), FACS (see, e.g., Mancuso et al., *Blood,* 97:3658-3661 (2001)), density gradient centrifugation (see, e.g., Baker et al., *Clin. Cancer Res.,* 13:4865-4871 (2003)), and depletion methods (see, e.g., Meye et al., *Int. J. Oncol.,* 21:521-530 (2002)).

In one embodiment, to preserve the in situ activation states, the signal transducers are advantageously extracted shortly after the cells are isolated, preferably within 96, 72, 48, 24, 6, or 1 hr, more preferably within 30, 15, or 5 minutes. The isolated cells may also be advantageously incubated with growth factors usually at nanomolar to micromolar concentrations for about 1-30 minutes to resuscitate or stimulate signal transducer activation (see, e.g., Irish et al., *Cell,* 118: 217-228 (2004)). Stimulatory growth factors include epidermal growth factor (EGF), heregulin (HRG), TGF-α, PIGF, angiopoietin (Ang), NRG1, PGF, TNF-α, VEGF, PDGF, IGF, FGF, HGF, cytokines, and the like. To evaluate potential anticancer therapies for an individual patient, prior to growth factor stimulation, the isolated cells can be incubated with one or more anticancer drugs of varying doses. Growth factor stimulation can be performed for a few minutes or hours (e.g., 1-5 minutes to 1-6 hours). The differential activation of signaling pathways with and without anticancer drugs aids in the selection of a suitable cancer therapy at the proper dose for each individual patient. After isolation, anticancer agent treatment, and/or growth factor stimulation, the cells are lysed to extract the signal transducers using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the lysate can be stored at −80° C. until use.

In some embodiments, the anticancer drug comprises an agent that interferes with the function of activated signal transduction pathway components in cancer cells. Non-limiting examples of such agents include those listed below:

TABLE A

| EGFR (A) (ErbB1) | Her 2 (C) (ErbB2) | Her 3 (ErbB3)(E) | Her4 (ErbB4) target |
|---|---|---|---|
| Cetuximab | Trastuzumab | Antibody (U3) | |
| Panitumumab | (Herceptin) | | |
| Matuzumab | Pertuzumab (DNA) | | |
| Nimotuzumab | BMS-599626 (Heterodimerization Her1/2; Phase 1) | | |
| EGFR vaccine | | | |
| EGFR (B) (ErbB1) | Her 2 (D) (ErbB2) | | |
| Erlotinib | CP-724714 (Pfizer) | | |
| Gefitinib | | | |
| EKB 569 (Wyeth, Irreversible, II CRC) | | | |
| CL-387-785 (Wyeth, Irreversible, Preclinical) | | | |
| ErbB1/2 (F) | | | |
| Lapatinib | | | |
| HKI-272 (Wyeth, Irreversible, I/II NSCLC, Breast) | | | |
| HKI-357 (Preclinical) | | | |
| BIBW 2992 (Boehringer Ingelheim, Irreversible, I/II Prostate, Ovarian, Breast) | | | |
| ErbB1/2/4 (G) | | | |
| Canertinib (Pfizer, Irreversible, II NSCLC, Breast) | | | |
| ARRY-334543 | | | |
| JNJ-26483327 | | | |
| JNJ-26483327 | | | |
| Raf (H) | SRC | | |
| Sorafenib | AZ | | |
| PLX4032 (Plexxikon) | | | |
| Mek: (I) | NFkB-IkB | | |
| PD-325901 (II: NSCLC) | | | |
| AZD6244 - Array/Az | | | |
| XL518 Exelisis/DNA | | | |
| mTor target (J) | | | |
| Rad 001: Everolimus (Novartis, combination with Gefetinib/Erlotinib; I/II: NSCLC, Glioblastoma) | | | |
| Temsirolimus (Wyeth, combination with Gefetinib/Erlotinib; I/II: NSCLC, Glioblastoma) | | | |
| AP-23573 (Ariad, I/II: Endometrial) | | | |
| PI3K: | | | |
| PX-866 (P110alpha specific inhibition; ProIX Pharma; Preclinical NSCLC) | | | |
| VEGF target (Targets VEGFR2, and VEGFR1) (K) | | | |
| Avastin (DNA) | | | |
| HuMV833 (PDL) anti-VEGFa | | | |
| VEGF-Trap - Regeneron/Aventis (Receptor mimic) (Phase 2) | | | |
| VEGFR-2 target (L) | EPH A-D | | |
| DC101 - Imclone (Phase 2/3?) | | | |
| IMC-IC11 Chimeric IgG1 against VEGFR2 | | | |

TABLE A-continued

Figure 3:
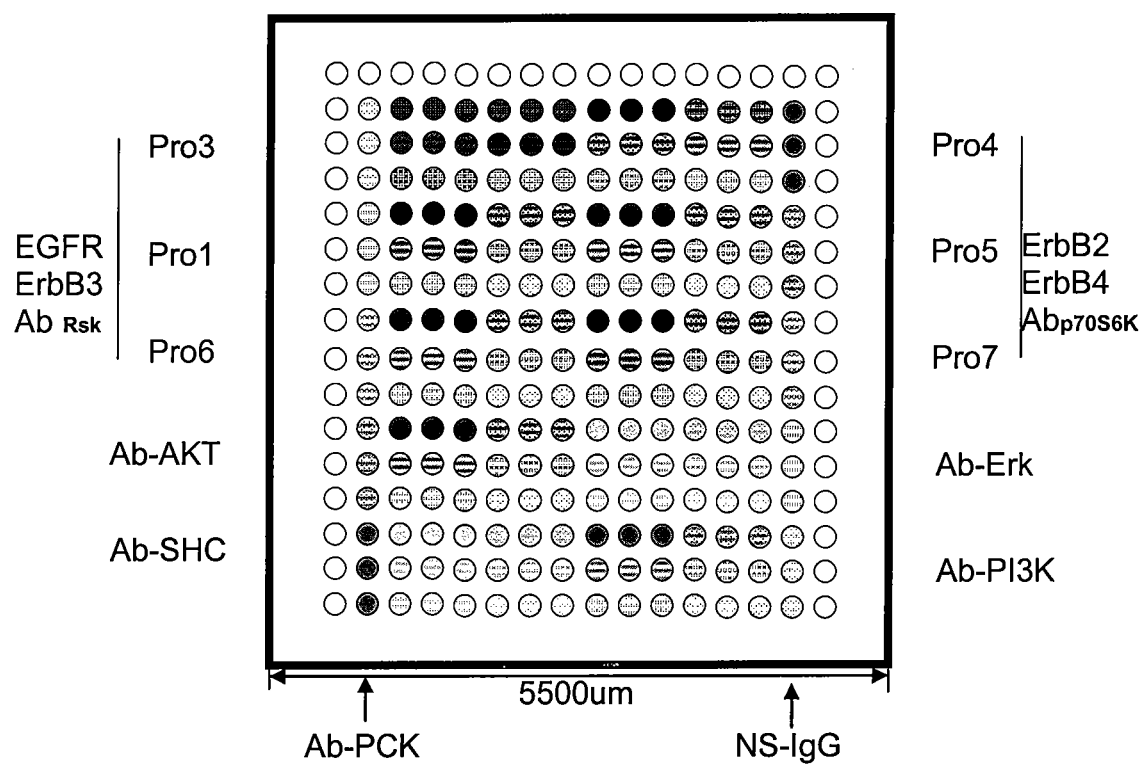
FIG. 3 shows a schematic example of an addressable array comprising dilutions of antibodies to components of a receptor tyrosine kinase pathway, such as those in the EGFR/MAPK/ERK pathway.
Figure 4:
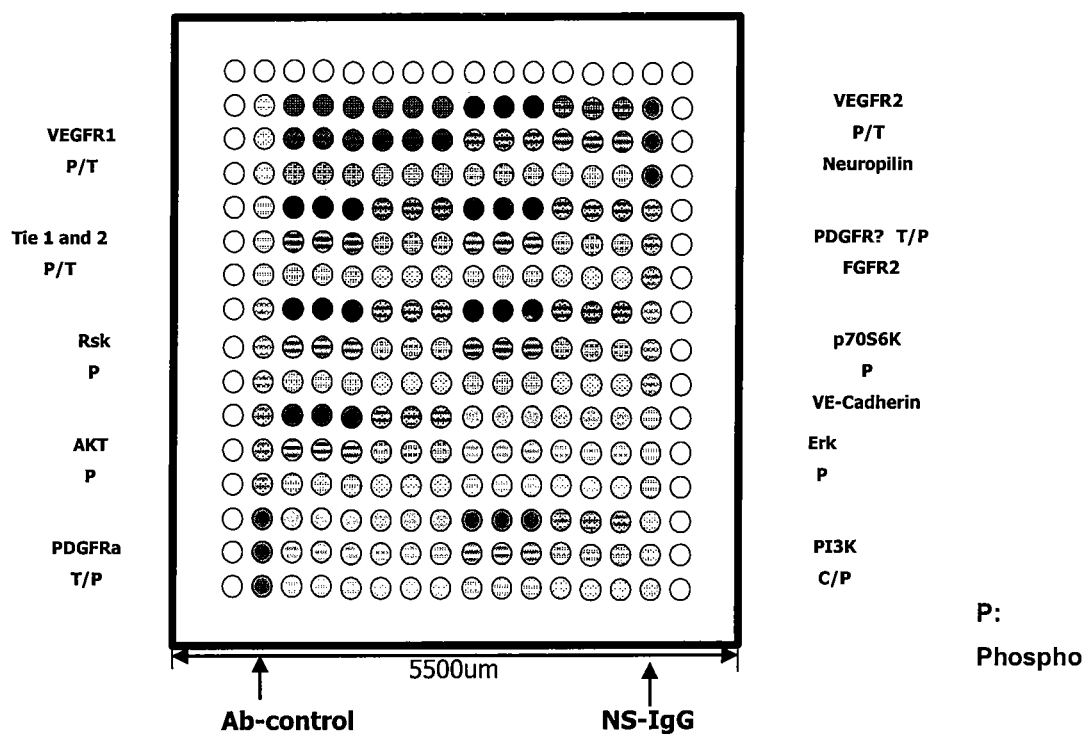
FIG. 4 shows a schematic example of an addressable array comprising dilutions of antibodies to components of signal transduction pathways activated in tumor angiogenesis.

IMC1121B Fully humanized
CDP-791 (Celltech, pegalated di-Fab antibody against R2
Pazopanib (GSK) (Multiple myeloma, ovarian, RCC Phase 3 enrollment completed, sarcoma II)
CDP-791 (UCB)
CP-547632 (OSI, PFIZER): (+ EGFR + PDGFR) (NSCLC, Ovarian Phase 2)
AG13736 (Pfizer): VEGFR1, 2 and PDGFRbeta) (RCC II)
E-7080 (Eisai)
CHIR-258 (VEGFR1, 2 FGFR3, PDGFR)
OSI-930 (+ cKit, PDGFR)
Bay-579352 (+ PDGFR)
ABT-869 (+CSF1R, Erk, Flt-3, PDGFR)
BMS-540215 (+FGFR1)
KRN-951
BBIW
VEGFR 1/2/3:
AZD 2171 (NSCLC, CRC)
AMG-706 (+ PDGFR)
VEGFR 2/ErbB1/2 (EGFR)/cMet/FGFR (M)
ZD6474 (vandetanib) (Phase III: thyroid, NSCLC)
XL647 (Exelixis; Also EPHB2): (Patient resistant to Erlotinib; Asian patients) (Phase 2)
AEE 788 (Novartis, Phase1/2)
VEGFR2/3/Raf/PDGFR/cKit/Flt-3 (N)     TIE 1/2
Sorafenib (RCC, HCC, NSCLC(III), Melanoma(III),
VEGFR2/1/3, Flt-3, cFMS, PDGFR/cKit/(O)   PDGFR target (P)
PTK787 (Not cFMS, FLT-3)                  Tandutinib
Sunitinib                                 Nilotinib
XL-999
SU-6668 (Pfizer)
GSK
AZ (AZD2171)
BMS
Novartis (AEE-788)
Amgen
Others
Abl target: (Q)    FTL 3    RET
Imatinib
Dasatinib
Nilotinib
AT-9283
AZD-0530
Bosutinib
Kit target (R)     HGFR1/2   FGFR1-4
AMG-706                      Chiron
XL-880
XL-999
IGF-1R Target (S)
Merck
Pfizer
Novartis
HSP90 inhibitors:
IPI-504 (Infinity Pharma, Mutant EGFR, I/II multiple myeloma, GIST)
17-AAG (Kosan, I/II solid tumors)
Anti-Mitotic Drugs:
Docetaxel (Microtubule stabilizer; Adjuvant and advanced Breast cancer; NSCLC, Androgen
independent Prostate cancer)
Paclitaxel (Microtubule stabilizer; Adjuvant and advanced Breast cancer; NSCLC, Ovarian cancer,
AIDS related Kaposi sarcoma)
Vinblastine, Vincristine, Vinorelbine (Microtubule De-stabilizers)
Other targets:
HDAC inhibitors
BCL2
Chemotherapeutics (breakdown)
Proteosome inhibitors In another embodiment, the present invention provides an addressable array having superior dynamic range comprising a plurality of dilution series of capture antibodies restrained on a solid support, in which the capture antibodies in each dilution series are specific for one or more analytes corresponding to a component of a signal transduction pathway. In various aspects, this embodiment includes arrays that comprise components of signal transduction pathways characteristic of particular tumors, e.g., signal transduction pathways active in lung cancer cells. Thus, the invention may be advantageously practiced wherein each type of cancer is represented on a single array or chip. In some aspects, the components of a given signal transduction pathway active in a particular tumor cell are arrayed in a linear sequence that corresponds to the sequence in which information is relayed through a signal transduction pathway within a cell. Examples of such arrays are shown in FIGS. 3 and 4.

Non-limiting examples of signal transduction pathways that may be interrogated using the present invention include those shown in Table 1.

TABLE 1

| | | | | | | | |
|---|---|---|---|---|---|---|---|
| Pathway 1 | EGFR | EGFR Phospho | EGFR Shc | EGFR ubiquitin | EGFR-PI3K | PTEN | |
| Pathway 2 | EGFR | EGFRVIII | EGFR Phospho | EGFR Shc | EGFR ubiquitin | EGFRVIII Phospho | PTEN |
| Pathway 3 | ERBB2 | ERBB2 Phospho | Her 2 Shc | ERBB2:PI3K Complex | ErbB2 ubiquitin | PTEN | |
| Pathway 4 | ERBB2 | P85Truncated ERBB2 | ERBB2 Phospho | P85Truncated ERBB2 Phospho | Her 2 Shc | ERBB2:PI3K Complex | ErbB2 ubiquitin |
| Pathway 5 | ERBB3 | ERBB3Phospho | ERBB3:PI3K Complex | ERBB3 PI3K Phospho | ERBB3:Shc | | |
| Pathway 6 | ERBB4 | ERBB4Phospho | ERBB4:Shc | | | | |
| Pathway 7 | IGF-1R | IGF-1RPhospho | IGF-1R:IRS | IRS:PI3K | Phospho IRS | IGF-1R:PI3K | |
| Pathway 8 | INSR | INSRPhospho | | | | | |
| Pathway 9 | KIT | KIT Phospho | | | | | |
| Pathway 10 | FLT3 | FLT3Phospho | | | | | |
| Pathway 11 | HGFR 1 | HGFR 1 Phospho | | | | | |
| Pathway 12 | HGFR 2 | HGFR 2 Phospho | | | | | |
| Pathway 13 | RET | RET Phospho | | | | | |
| Pathway 14 | PDGFR alpha | PDGFR alpha Phospho | | | | | |
| Pathway 15 | PDGFR beta | PDGFR beta Phospho | | | | | |
| Pathway 16 | VEGFR 1 | VEGFR 1 Phospho | VEGFR 1: PLCγcomplex | VEGFR 1: Src | | | |
| Pathway 17 | VEGFR 2 | VEGFR 2 Phospho | VEGFR 2: PLCγ complex | VEGFR 2: Src | VEGFR-2/heparin sulphate complex | VEGFR-2, VE-cadherin complex | |
| Pathway 18 | VEGFR 3 | VEGFR 3 Phospho | | | | | |
| Pathway 19 | FGFR 1 | FGFR 1 Phospho | | | | | |
| Pathway 20 | FGFR 2 | FGFR 2 Phospho | | | | | |
| Pathway 21 | FGFR 3 | FGFR 3 Phospho | | | | | |
| Pathway 22 | FGFR 4 | FGFR 4 Phospho | | | | | |
| Pathway 23 | TIE 1 | TIE 1 Phospho | | | | | |
| Pathway 24 | TIE 2 | TIE 2 Phospho | | | | | |
| Pathway 25 | EPHA | EPHA Phospho | | | | | |
| Pathway 26 | EPHB | EPHB Phospho | | | | | |
| Pathway 27 | NFkB-IkB complex | phospho-IκB (S32) Total IkB | Total NFκB Phospho NFκB(S536) | Total P65 IkBa Phospho P65 IkBa | | | |
| Pathway 28 | ER | Phospho ER | ER-AIB1 | Other ER complexes | | | |
| Pathway 29 | PR | Phospho Pr | | PR complexes | | | |
| Pathway 30 | Hedgehog Pathway | | | | | | |
| Pathway 31 | Wnt pathway | | | | | | |
| Pathway 32 | Notch Pathway | | | | | | |
| Pathway 33 | Total Mek Phospho Mek (S217/S221) | Total Erk Phospho Erk (T202/Y204) | Total Rsk-1 Phospho Rsk-1 (T357/S363) | Total Stat3 Phospho Stat-3 (Y705) (S727) Total Stat 1 Phospho Stat1 (Y 701) | Phospho Bad (S112) Bad (total) | Total Fak Phospho Fak (Y576) | Total cSrc Phospho cSrc(Y416) | Total Ras Phospho Ras |
| Pathway 34 | Akt (Total) Phospho Akt (T473) | Phospho Akt (T308) | Phospho Bad (S112) Bad (total) | Phospho Bad (S136) | Bad:14-3-3 complex | Total mTor Phospho mTor (S2448) | Total p70S6K Phospho p70S6K (T229) (T389) | GSK3beta Total (Phospho Ser 9) |

TABLE 1-continued

| Pathway 35 | Total Jnk Phospho Jnk (T183/Y185) | Total P38 Phospho P38 (T180/Y182) | Total Rb Phospho Rb (S249/T252) Phospho Rb (S780) | Total p53 Phospho p53 (S392) Phospho p53 (S20) | phospho-CREB(S133) Total CREB | Total c-Jun phospho-c-Jun; (S63) | Total Paxillin Phospho Paxillin (Y118) |
|---|---|---|---|---|---|---|---|
| Pathway 36 | Ki67 | Cleaved Caspase 3, 8, 9 others | | | | | |
| Pathway 37 | TGFbeta | | | | | | |

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a radiotherapeutic agent; a vaccine; and/or any other compound with the ability to reduce or abrogate the uncontrolled growth of aberrant cells such as cancerous cells. In some embodiments, the isolated circulating cells are treated with an anti-signaling agent and/or an anti-proliferative agent in combination with one or more chemotherapeutic agents.

Examples of anti-signaling agents suitable for use in the present invention include, without limitation, monoclonal antibodies such as trastuzumab (Herceptin®), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016), canertinib (CI 1033), semaxinib (SU5416), vatalanib (PTK787/ZK222584), sorafenib (BAY 43-9006; Nexavar®), imatinib mesylate (Gleevec®), leflunomide (SU101), and vandetanib (ZACTIMA™; ZD6474); and combinations thereof.

Exemplary anti-proliferative agents include mTOR inhibitors such as sirolimus (rapamycin), temsirolimus (CCI-779), and everolimus (RAD001); Akt inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)methyl)-4-piperidinyl)-2H-benzimidazol-2-one, 10-(4'-(N-diethylamino)butyl)-2-chlorophenoxazine, 3-formylchromone thiosemicarbazone (Cu (II) Cl$_2$ complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125:1144-1145 (2003) and Kau et al., *Cancer Cell*, 4:463-476 (2003); and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Non-limiting examples of cancer vaccines useful in the present invention include, but are not limited to, ANYARA from Active Biotech, DCVax-LB from Northwest Biotherapeutics, EP-2101 from IDM Pharma, GV1001 from Pharmexa, 10-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto the array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.).

In some embodiments, the cellular extract comprises an extract of circulating cells of a solid tumor. The circulating cells are typically isolated from a patient sample using one or more separation methods known in the art including, for example, immunomagnetic separation, the CellTrack™ System, microfluidic separation, FACS, density gradient centrifugation, and depletion methods.

In other embodiments, the patient sample comprises a whole blood, serum, plasma, sputum, bronchial lavage fluid, urine, nipple aspirate, lymph, saliva, and/or fine needle aspirate sample. In certain instances, the whole blood sample is separated into a plasma or serum fraction and a cellular fraction (i.e., cell pellet). The cellular fraction typically contains red blood cells, white blood cells, and/or circulating cells of a solid tumor such as CTCs, CECs, CEPCs, disseminated tumor cells of the lymph node, and/or CSCs. The plasma or serum fraction usually contains, inter alia, nucleic acids (e.g., DNA, RNA) and proteins that are released by circulating cells of a solid tumor.

In some instances, the isolated circulating cells can be stimulated in vitro with one or more growth factors before, during, and/or after incubation with one or more anticancer drugs of interest. Stimulatory growth factors are described above. In other instances, the isolated circulating cells can be lysed, e.g., following growth factor stimulation and/or anticancer drug treatment, to produce the cellular extract (e.g., cell lysate) using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the cell lysate can be stored at −80° C. until use.

In preferred embodiments, the expression and/or activation states of a plurality of signal transduction molecules in tumor cells such as circulating cells of a solid tumor are detected using a single detection or proximity dual detection assay as described below.

IV. Construction of Antibody Arrays

In certain aspects, the activation state of a plurality of signal transduction molecules in a cellular extract of tumor cells such as circulating cells of a solid tumor is detected using an antibody-based array comprising a dilution series of capture antibodies restrained on a solid support. The arrays typically comprise a plurality of different capture antibodies at a range of capture antibody concentrations that are coupled to the surface of the solid support in different addressable locations.

The solid support can comprise any suitable substrate for immobilizing proteins. Examples of solid supports include, but not limited to, glass (e.g., a glass slide), plastic, chips, pins, filters, beads, paper, membranes, fiber bundles, gels, metal, ceramics, and the like. Membranes such nylon (Biotrans™, ICN Biomedicals, Inc. (Costa Mesa, Calif.); Zeta-Probe®, Bio-Rad Laboratories (Hercules, Calif.)), nitrocellulose (Protran®, Whatman Inc. (Florham Park, N.J.)), and PVDF (Immobilon™, Millipore Corp. (Billerica, Mass.)) are suitable for use as solid supports in the arrays of the present invention. Preferably, the capture antibodies are restrained on glass slides coated with a nitrocellulose polymer, e.g., FAST® Slides, which are commercially available from Whatman Inc. (Florham Park, N.J.).

Particular aspects of the solid support which are desirable include the ability to bind large amounts of capture antibodies and the ability to bind capture antibodies with minimal denaturation. Another suitable aspect is that the solid support displays minimal "wicking" when antibody solutions containing capture antibodies are applied to the support. A solid support with minimal wicking allows small aliquots of capture antibody solution applied to the support to result in small, defined spots of immobilized capture antibody.

The capture antibodies are typically directly or indirectly (e.g., via capture tags) restrained on the solid support via covalent or noncovalent interactions (e.g., ionic bonds, hydrophobic interactions, hydrogen bonds, Van der Waals forces, dipole-dipole bonds). In some embodiments, the capture antibodies are covalently attached to the solid support using a homobifunctional or heterobifunctional crosslinker using standard crosslinking methods and conditions. Suitable crosslinkers are commercially available from vendors such as, e.g., Pierce Biotechnology (Rockford, Ill.).

Methods for generating arrays suitable for use in the present invention include, but are not limited to, any technique used to construct protein or nucleic acid arrays. In some embodiments, the capture antibodies are spotted onto an array using a microspotter, which are typically robotic printers equipped with split pins, blunt pins, or ink jet printing. Suitable robotic systems for printing the antibody arrays described herein include the PixSys 5000 robot (Cartesian Technologies; Irvine, Calif.) with ChipMaker2 split pins (TeleChem International; Sunnyvale, Calif.) as well as other robotic printers available from BioRobics (Woburn, Mass.) and Packard Instrument Co. (Meriden, Conn.). Preferably, at least 2, 3, 4, 5, or 6 replicates of each capture antibody dilution are spotted onto the array.

Another method for generating arrays suitable for use in the present invention comprises dispensing a known volume of a capture antibody dilution at each selected array position by contacting a capillary dispenser onto a solid support under conditions effective to draw a defined volume of liquid onto the support, wherein this process is repeated using selected capture antibody dilutions at each selected array position to create a complete array. The method may be practiced in forming a plurality of such arrays, where the solution-depositing step is applied to a selected position on each of a plurality of solid supports at each repeat cycle. A further description of such a method can be found, e.g., in U.S. Pat. No. 5,807,522.

In certain instances, devices for printing on paper can be used to generate the antibody arrays. For example, the desired capture antibody dilution can be loaded into the printhead of a desktop jet printer and printed onto a suitable solid support (see, e.g., Silzel et al., *Clin. Chem.*, 44:2036-2043 (1998)).

In some embodiments, the array generated on the solid support has a density of at least about 5 spots/cm$^2$, and preferably at least about 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000, or 10,000 spots/cm$^2$.

In certain instances, the spots on the solid support each represents a different capture antibody. In certain other instances, multiple spots on the solid support represent the same capture antibody, e.g., as a dilution series comprising a series of descending capture antibody concentrations.

Additional examples of methods for preparing and constructing antibody arrays on solid supports are described in U.S. Pat. Nos. 6,197,599, 6,777,239, 6,780,582, 6,897,073, 7,179,638, and 7,192,720; U.S. Patent Publication Nos. 20060115810, 20060263837, 20060292680, and 20070054326; and Varnum et al., *Methods Mol. Biol.*, 264: 161-172 (2004).

Methods for scanning antibody arrays are known in the art and include, without limitation, any technique used to scan protein or nucleic acid arrays. Microarray scanners suitable for use in the present invention are available from PerkinElmer (Boston, Mass.), Agilent Technologies (Palo Alto, Calif.), Applied Precision (Issaquah, Wash.), GSI Lumonics Inc. (Billerica, Mass.), and Axon Instruments (Union City, Calif.). As a non-limiting example, a GSI ScanArray3000 for fluorescence detection can be used with ImaGene software for quantitation.

V. Single Detection Assays

In some embodiments, the assay for detecting the activation state of a particular analyte (e.g., signal transduction molecule) of interest in a cellular extract of tumor cells such as circulating cells of a solid tumor is a multiplex, high-throughput two-antibody assay having superior dynamic range. As a non-limiting example, the two antibodies used in the assay can comprise: (1) a capture antibody specific for the analyte; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody comprises an activation state-independent antibody, which detects the total amount of the analyte in the cellular extract. The activation state-independent antibody is generally capable of detecting both the activated and non-activated forms of the analyte.

In a preferred embodiment, the two-antibody assay comprises:
(i) incubating the cellular extract with a plurality of dilution series of capture antibodies to form a plurality of captured analytes;
(ii) incubating the plurality of captured analytes with activation state-dependent antibodies specific for the corresponding analytes to form a plurality of detectable captured analytes;
(iii) incubating the plurality of detectable captured analytes with first and second members of a signal amplification pair to generate an amplified signal; and
(iv) detecting the amplified signal generated from the first and second members of the signal amplification pair.

The two-antibody assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies and detection antibodies are preferably selected to minimize competition between them with respect to analyte binding (i.e., both capture and detection antibodies can simultaneously bind their corresponding signal transduction molecules).

In one embodiment, the detection antibodies comprise a first member of a binding pair (e.g., biotin) and the first member of the signal amplification pair comprises a second member of the binding pair (e.g., streptavidin). The binding pair members can be coupled directly or indirectly to the detection antibodies or to the first member of the signal amplification pair using methods well-known in the art. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

An exemplary protocol for performing the two-antibody assays described herein is provided in Example 3.

In another embodiment, the present invention provides kits for performing the two-antibody assays described above comprising: (a) a dilution series of a plurality of capture antibodies restrained on a solid support; and (b) a plurality of detection antibodies (e.g., activation state-independent antibodies and/or activation state-dependent antibodies). In some instances, the kits can further contain instructions for methods of using the kit to detect the activation states of a plurality of signal transduction molecules of circulating cells of a solid tumor. The kits may also contain any of the additional reagents described above with respect to performing the specific methods of the present invention such as, for example, first and second members of the signal amplification pair, tyramide signal amplification reagents, wash buffers, etc.

VI. Proximity Dual Detection Assays

In some embodiments, the assay for detecting the activation state of a particular analyte (e.g., signal transduction molecule) of interest in a cellular extract of tumor cells such as circulating cells of a solid tumor is a multiplex, high-throughput proximity (i.e., three-antibody) assay having superior dynamic range. As a non-limiting example, the three antibodies used in the proximity assay can comprise: (1) a capture antibody specific for the analyte; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, for example, the phosphorylation, ubiquitination, and/or complexation state of the analyte. The activation state-dependent antibody is generally capable of detecting both the activated and non-activated forms of the analyte.

In a preferred embodiment, the proximity assay comprises:
(i) incubating the cellular extract with a plurality of dilution series of capture antibodies to form a plurality of captured analytes;
(ii) incubating the plurality of captured analytes with detection antibodies comprising a plurality of activation state-independent antibodies and a plurality of activation state-dependent antibodies specific for the corresponding analytes to form a plurality of detectable captured analytes,
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(iii) incubating the plurality of detectable captured analytes with a second member of the signal amplification pair to generate an amplified signal; and
(iv) detecting the amplified signal generated from the first and second members of the signal amplification pair.

Alternatively, the activation state-dependent antibodies can be labeled with a facilitating moiety and the activation state-independent antibodies can be labeled with a first member of a signal amplification pair.

The proximity assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies, activation state-independent antibodies, and activation state-dependent antibodies are preferably selected to minimize competition between them with respect to analyte binding (i.e., all antibodies can simultaneously bind their corresponding signal transduction molecules).

In some embodiments, the activation state-independent antibodies further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor® 647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well-known in the art.

In certain instances, the activation state-independent antibodies are directly labeled with the facilitating moiety. The facilitating moiety can be coupled to the activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, the activation state-independent antibodies are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is between 1-10° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-reactivity between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, the activation state-dependent antibodies are directly labeled with the first member of the signal amplification pair. The signal amplification pair member can be coupled to the activation state-dependent antibodies using methods well-known in the art. In certain other instances, the activation state-dependent antibodies are indirectly labeled with the first member of the signal amplification pair via binding between a first member of a binding pair conjugated to the activation state-dependent antibodies and a second member of the binding pair conjugated to the first member of the signal amplification pair. The binding pair members (e.g., biotin/streptavidin) can be coupled to the signal amplification pair member or to the activation state-dependent antibodies using methods well-known in the art. Examples of signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azinobis(3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, olefin-, thioether-, and selenoether-protecting groups. Additional photosensitizers and protected hapten molecules suitable for use in the proximity assays of the present invention are described in U.S. Pat. No. 5,807, 675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, β-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

An exemplary protocol for performing the proximity assays described herein is provided in Example 4.

In another embodiment, the present invention provides kits for performing the proximity assays described above comprising: (a) a dilution series of a plurality of capture antibodies restrained on a solid support; and (b) a plurality of detection antibodies (e.g., activation state-independent antibodies and activation state-dependent antibodies). In some instances, the kits can further contain instructions for methods of using the kit to detect the activation states of a plurality of signal transduction molecules of circulating cells of a solid tumor. The kits may also contain any of the additional reagents described above with respect to performing the specific methods of the present invention such as, for example, first and second members of the signal amplification pair, tyramide signal amplification reagents, substrates for the facilitating moiety, wash buffers, etc.

VII. Production of Antibodies

The generation and selection of antibodies not already commercially available for analyzing the activation states of signal transduction molecules in tumor cells such as rare circulating cells in accordance with the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); *Solid Phase Peptide Synthesis*, Greg B. Fields, ed., *Meth. Enzymol.*, Vol. 289 (1997); Kiso et al., *Chem. Pharm. Bull.*, 38:1192-99 (1990); Mostafavi et al., *Biomed. Pept. Proteins Nucleic Acids*, 1:255-60, (1995); and Fujiwara et al., *Chem. Pharm. Bull.*, 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., *Antibody Engineering: A Practical Approach*, Borrebaeck, Ed., Oxford University Press, Oxford (1995); and Huse et al., *J. Immunol.*, 149:3914-3920 (1992).

In addition, numerous publications have reported the use of phage display technology to produce and screen libraries of polypeptides for binding to a selected target antigen (see, e.g., Cwirla et al., *Proc. Natl. Acad. Sci. USA*, 87:6378-6382 (1990); Devlin et al., *Science*, 249:404-406 (1990); Scott et al., *Science*, 249:386-388 (1990); and Ladner et al., U.S. Pat. No. 5,571,698). A basic concept of phage display methods is the establishment of a physical association between a polypeptide encoded by the phage DNA and a target antigen. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target antigen bind to the target antigen and these phage are enriched by affinity screening to the target antigen. The identity of polypeptides displayed from these phage can be determined from their respective genomes. Using these methods, a polypeptide identified as having a binding affinity for a desired target antigen can then be synthesized in bulk by conventional means (see, e.g., U.S. Pat. No. 6,057,098).

The antibodies that are generated by these methods can then be selected by first screening for affinity and specificity with the purified polypeptide antigen of interest and, if required, comparing the results to the affinity and specificity of the antibodies with other polypeptide antigens that are desired to be excluded from binding. The screening procedure can involve immobilization of the purified polypeptide antigens in separate wells of microtiter plates. The solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized polypeptide antigen is present.

The antibodies so identified can then be further analyzed for affinity and specificity. In the development of immunoassays for a target protein, the purified target protein acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody may be a more important measure than absolute affinity and specificity of that antibody.

Those skilled in the art will recognize that many approaches can be taken in producing antibodies or binding fragments and screening and selecting for affinity and specificity for the various polypeptides of interest, but these approaches do not change the scope of the present invention.

A. Polyclonal Antibodies

Polyclonal antibodies are preferably raised in animals by multiple subcutaneous (sc) or intraperitoneal (ip) injections of a polypeptide of interest and an adjuvant. It may be useful to conjugate the polypeptide of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R_1N\!\!=\!\!C\!\!=\!\!NR$, wherein R and $R_1$ are different alkyl groups.

Animals are immunized against the polypeptide of interest or an immunogenic conjugate or derivative thereof by combining, e.g., 100 µg (for rabbits) or 5 µg (for mice) of the antigen or conjugate with 3 volumes of Freund's complete adjuvant and injecting the solution intradermally at multiple sites. One month later, the animals are boosted with about ⅕ to ⅒ the original amount of polypeptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same polypeptide, but conjugation to a different immunogenic protein and/or through a different cross-linking reagent may be used. Conjugates can also be made in recombinant cell culture as fusion proteins. In certain instances, aggregating agents such as alum can be used to enhance the immune response.

B. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., Nature, 256:495 (1975) or by any recombinant DNA method known in the art (see, e.g., U.S. Pat. No. 4,816, 567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.*, 133:3001 (1984); and Brodeur et al., *Monoclonal Antibody Production Techniques and Applications*, Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.*, 5:256-262 (1993); and Pluckthun, *Immunol Rev.*, 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA*, 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature*, 348:552-554 (1990); Clackson et al., *Nature*, 352:624-628 (1991); and Marks et al., *J. Mol. Biol.*, 222:581-597 (1991). The production of high affinity (nM range) human monoclonal antibodies by chain shuffling is described in Marks et al., *BioTechnology*, 10:779-783 (1992). The use of combinatorial infection and in vivo recombination as a strategy for constructing very large phage libraries is described in Waterhouse et al., *Nuc. Acids Res.*, 21:2265-2266 (1993). Thus, these techniques are viable alternatives to traditional monoclonal antibody hybridoma methods for the generation of monoclonal antibodies.

C. Humanized Antibodies

Methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed by substituting the hypervariable region sequences of a non-human antibody for the corresponding sequences of a human antibody. See, e.g., Jones et al., *Nature*, 321:522-525 (1986); Riechmann et al., *Nature*, 332:323-327 (1988); and Verhoeyen et al., *Science*, 239: 1534-1536 (1988). Accordingly, such "humanized" antibodies are chimeric antibodies (see, e.g., U.S. Pat. No. 4,816, 567), wherein substantially less than an intact human variable domain has been substituted by the corresponding sequence from a non-human species. In practice, humanized antibodies are typically human antibodies in which some hypervariable region residues and possibly some framework region (FR) residues are substituted by residues from analogous sites of rodent antibodies.

The choice of human variable domains, both light and heavy, to be used in making the humanized antibodies described herein is an important consideration for reducing antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (see, e.g., Sims et al., *J. Immunol.*, 151: 2296 (1993); and Chothia et al., *J. Mol. Biol.*, 196:901 (1987)). Another method uses a particular FR derived from the consensus sequence of all human antibodies of a particular subgroup of light or heavy chains. The same FR may be used for several different humanized antibodies (see, e.g., Carter et al., *Proc. Natl. Acad. Sci. USA*, 89:4285 (1992); and Presta et al., *J. Immunol.*, 151:2623 (1993)).

It is also important that antibodies be humanized with retention of high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and specifically involved in influencing antigen binding.

Various forms of humanized antibodies are contemplated in accordance with the present invention. For example, the humanized antibody can be an antibody fragment, such as a Fab fragment. Alternatively, the humanized antibody can be an intact antibody, such as an intact IgA, IgG, or IgM antibody.

D. Human Antibodies

As an alternative to humanization, human antibodies can be generated. In some embodiments, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immun.*, 7:33 (1993); and U.S. Pat. Nos. 5,591,669, 5,589, 369, and 5,545,807.

Alternatively, phage display technology (see, e.g., McCafferty et al., *Nature*, 348:552-553 (1990)) can be used to produce human antibodies and antibody fragments in vitro, using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats as described in, e.g., Johnson et al., *Curr. Opin. Struct. Biol.*, 3:564-571 (1993). Several sources of V-gene segments can be used for phage display. See, e.g., Clackson et al., *Nature*, 352:624-628 (1991). A repertoire of V genes from unimmunized human donors can be constructed and antibodies to a diverse array of antigens (including self-antigens) can be isolated essentially following the techniques described in Marks et al., *J. Mol. Biol.*, 222:581-597 (1991); Griffith et al., *EMBO J.*, 12:725-734 (1993); and U.S. Pat. Nos. 5,565,332 and 5,573,905.

In certain instances, human antibodies can be generated by in vitro activated B cells as described in, e.g., U.S. Pat. Nos. 5,567,610 and 5,229,275.

E. Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.*, 24:107-117 (1992); and Brennan et al., *Science*, 229:81 (1985)). However, these fragments can now be produced directly using recombinant host cells. For example, the antibody fragments can be isolated from the antibody phage libraries discussed above. Alternatively, Fab'-SH fragments can be directly recovered from *E. coli* cells and chemically coupled to form F(ab')$_2$ fragments (see, e.g., Carter et al., *BioTechnology*, 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

F. Bispecific Antibodies

Bispecific antibodies are antibodies that have binding specificities for at least two different epitopes. Exemplary bispecific antibodies may bind to two different epitopes of the same polypeptide of interest. Other bispecific antibodies may combine a binding site for the polypeptide of interest with binding site(s) for one or more additional antigens. Bispecific antibodies can be prepared as full-length antibodies or antibody fragments (e.g., F(ab')$_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see, e.g., Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., *Meth. Enzymol.*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., *Science*, 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from *E. coli* and chemically coupled to form bispecific antibodies. For example, a fully humanized bispecific antibody F(ab')$_2$ molecule can be produced by the methods described in Shalaby et al., *J. Exp. Med.*, 175: 217-225 (1992). Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., *J. Immunol.*, 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.*, 152:5368 (1994).

Antibodies with more than two valencies are also contemplated. For example, trispecific antibodies can be prepared. See, e.g., Tutt et al., *J. Immunol.*, 147:60 (1991).

G. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.*, 10: 163-167 (1992) describes a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.*, 62:1-13 (1983)). Protein G is recommended for all mouse isotypes and for human γ3 (see, e.g., Guss et al., *EMBO J.*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

One of skill in the art will appreciate that any binding molecule having a function similar to an antibody, e.g., a binding molecule or binding partner which is specific for one or more analytes of interest in a sample, can also be used in the methods and compositions of the present invention. Examples of suitable antibody-like molecules include, but are not limited to, domain antibodies, unibodies, nanobodies, shark antigen reactive proteins, avimers, adnectins, anticalms, affinity ligands, phylomers, aptamers, affibodies, trinectins, and the like.

VIII. Methods of Administration

According to the methods of the present invention, the anticancer drugs described herein are administered to a subject by any convenient means known in the art. The methods of the present invention can be used to select a suitable anticancer drug or combination of anticancer drugs for the treatment of a tumor (e.g., lung tumor) in a subject. In addition, the methods of the invention can be used to select a subject having a tumor (e.g., lung tumor) who is a suitable candidate for treatment with an anticancer drug or combination of anticancer drugs. The methods of the invention can also be used to identify the response of a tumor (e.g., lung tumor) in a subject to treatment with an anticancer drug or combination of anticancer drugs. In addition, the methods of the invention can be used to predict the response of a subject having a tumor (e.g., lung tumor) to treatment with an anticancer drug or combination of anticancer drugs. One skilled in the art will appreciate that the anticancer drugs described herein can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a radiotherapeutic agent; a vaccine; and/or any other compound with the ability to reduce or abrogate the uncontrolled growth of aberrant cells such as cancerous cells. In some embodiments, the subject is treated with an anti-signaling agent and/or an anti-proliferative agent in combination with one or more chemotherapeutic agents. Exemplary monoclonal antibodies, tyrosine kinase inhibitors, anti-proliferative agents, chemotherapeutic agents, radiotherapeutic agents, and vaccines are described above.

The anticancer drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the anticancer drugs described herein can be co-administered with conventional immunotherapeutic agents including, but not limited to, immunostimulants (e.g., Bacillus Calmette-Guérin (BCG), levamisole, interleukin-2, alpha-interferon, etc.), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" includes physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., *Remington's Pharmaceutical Sciences,* 18th Ed., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *Remington's Pharmaceutical Sciences,* supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the activation states of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

In certain other instances, the methods of performing multiplexed high-throughput immunoassays and protein arrays are disclosed in WO 2008/036802 incorporated herein by reference. The application discloses inter alia, antibody-based arrays for detecting the activation state and/or total amount of a plurality of signal transduction molecules in rare circulating cells and methods of using the arrays for facilitating cancer prognosis and diagnosis and the design of personalized, targeted therapies. The application further discloses a support surface comprising a plurality of capture molecules restrained in an "addressable" or "zip code" array. Each distinct region of the array comprises a unique capture agent that specifically binds the capture tag present on the activation state-independent detection antibody or the activation state-dependent antibody, thereby restraining and organizing the tagged detection antibodies in the array. In a preferred embodiment, the capture agents and capture tags are oligonucleotides that specifically hybridize to each other.

IX. Examples

The following examples are offered to illustrate, but not to limit, the claimed invention.

Example 1

Isolation, Stimulation, and Lysis of Circulating Cells

Circulating cells of a solid tumor comprise cells that have either metastasized or micrometastasized from a solid tumor and include circulating tumor cells (CTCs), cancer stem cells (CSCs), and/or cells that are migrating to the tumor (e.g., circulating endothelial progenitor cells (CEPCs), circulating endothelial cells (CECs), circulating pro-angiogenic myeloid cells, circulating dendritic cells, etc.). Patient samples containing circulating cells can be obtained from any accessible biological fluid (e.g., blood, urine, nipple aspirate, lymph, saliva, fine needle aspirate, etc.). The circulating cells can be isolated from a patient sample using one or more separation methods such as, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the CellTrack™ System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

Manual Isolation of CTCs:
Immunomagnetic separation of CTCs—manual isolation followed by an activation assay:
1) Magnetic beads (Dynal M450; Dynal AS; Oslo, Norway) that have been previously conjugated to an anti-EpCAM monoclonal antibody (Kordia Life Sciences; Leiden, The Netherlands) are used.
2) Just prior to use, the pre-coated Dynabeads are washed once in an equal volume of PBS with BSA at 0.01%.
3) 25 µl of the pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Peripheral blood from human subjects is drawn in a siliconized tube containing 1 mg/ml EDTA. The first 3-5 ml is discarded to avoid contamination with epithelial cells released from the punctured vein.
2) 1 ml of whole blood is diluted 1:3 with 0.9% NaCl prior to use.

Control preparation:
1) Cell line controls are made by spiking human cancer cell lines into HL-60 cells.
2) Cell line controls are used at a concentration of $2.5 \times 10^6$ cells/ml.

Manual Isolation of CECs and CEPCs:

As a non-limiting example, viable CECs and CEPCs can be isolated using the immunomagnetic isolation/enrichment technique described in Beerepoot et al., *Ann. Oncology*, 15:139-145 (2004). Briefly, peripheral blood is incubated with magnetic beads (Dynal M450 $IgG_1$) that have been previously conjugated to an anti-CD146 monoclonal antibody (Kordia Life Sciences). This antibody recognizes all lineages of endothelial cells, but not hematopoetic or epithelial cells, in peripheral blood (George et al., *J. Immunol. Meth.*, 139: 65-75 (1991)). Negative selection of hematopoetic and epithelial cells can be used prior to the positive selection with magnetic beads conjugated to appropriate antibodies (e.g., Dynal-CD45 beads for depleting leukocytes, Dynal-CD14 beads for depleting monocytes, Dynal-EpCAM for depleting epithelial cells (Invitrogen; Carlsbad, Calif.)). In this example, only positive selection is used.

Immunomagnetic separation of CECs and CEPCs—manual isolation followed by an activation assay:
1) Magnetic beads (Dynal M450) that have been previously conjugated to an anti-CD 146 monoclonal antibody (Kordia Life Sciences) are used.
2) Just prior to use, the pre-coated Dynabeads are washed once in an equal volume of PBS with BSA at 0.01%.
3) 25 μl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 μl of stimulation buffer.

Sample preparation:
1) Peripheral blood from human subjects is drawn in a siliconized tube containing 1 mg/ml EDTA. The first 3-5 ml is discarded to avoid contamination with endothelial cells released from the punctured vein.
2) 1 ml of whole blood is diluted 1:3 with 0.9% NaCl prior to use.

Control preparation:
1) Cell line controls are made by spiking human umbilical vein endothelial cells (HUVEC) into HL-60 cells.
2) Cell line controls are used at a concentration of $2.5 \times 10^6$ cells/ml.

Manual Isolation of CEPCs (Without CECs):

CEPCs are a circulating subtype of bone marrow-derived progenitor cells that have the capacity of differentiating into mature endothelial cells in response to various angiogenic growth factors. CEPCs may be isolated by selection with antibodies recognizing the surface marker CD34. CD133 is a surface marker that differentiates immature endothelial progenitor cells (EPCs) or primitive hematopoetic stem cells (HSCs) from CEPCs. Various isolation procedures of CEPCs from different sources have been described using adherence culture or magnetic microbeads. In this example, a protocol modified from that described in Asahara et al., *Science,* 275: 964-967 (1997) is used.

Immunomagnetic separation of CEPCs—manual isolation followed by an activation assay:
1) Magnetic beads (Dynal M450 CD34) are used. These beads are coated with a monoclonal antibody specific for the CD34 surface antigen.
2) Just prior to use, the pre-coated Dynabeads are washed once in an equal volume of PBS with BSA at 0.01%.
3) 25 μl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 μl of stimulation buffer.

Sample preparation:
1) Peripheral blood from human subjects is drawn in a siliconized tube containing 1 mg/ml EDTA. The first 3-5 ml is discarded to avoid contamination with endothelial cells released from the punctured vein.
2) 10 ml of blood is diluted 1:1 with a balanced salt solution.
3) 4 ml of diluted blood is layered onto 3 ml of Ficoll-Paque in 10 ml tubes.
4) Tubes are spun at 400×g for 30-40 min at 18-20° C.
5) The upper layer containing plasma and platelets is drawn off using a sterile Pasteur pipette, leaving the layer of mononuclear cells undisturbed at the interface.
6) The mononuclear cells are transferred to a sterile centrifuge tube using a sterile pipette.
7) 6 ml of balanced salt solution is added and the cells are gently resuspended.
8) The mixture is centrifuged at 60-100×g for 10 min at 18-20° C.
9) The supernatant is removed and the mononuclear cells from each tube are resuspended in 1 ml PBS.

Cell Isolation of CTCs, CECs, and CEPCs Using the Veridex System:

Veridex (Warren, N.J.) has commercialized the CellSearch system, which consists of a CellPrep system, the CellSearch Epithelial Cell Kit, and the CellSpotter Analyzer. The CellPrep system is a semi-automated sample preparation system (Kagan et al., *J. Clin. Ligand Assay,* 25:104-110 (2002)). The CellSearch Epithelial Cell Kit consists of: ferrofluids coated with anti-EpCAM antibodies specific for epithelial cells; phycoerythrin-conjugated antibodies to cytokeratins 8, 18, and 19; an anti-CD45 antibody conjugated to allophycocyanin; DAPI dye; and buffers for washing, permeabilizing, and resuspending the cells. The protocol used in this example is also described in Allard et al., *Clin. Cancer Res.,* 10:6897-6904 (2004). The entire Veridex system can be used for CTC enumeration or, by removing the sample manually after isolation with the CellPrep system, can provide a method of isolation prior to analysis for pathway activation. The number of CTCs can be informative for algorithm development.

Veridex system—CTC enrichment followed by enumeration:
1) 7.5 ml of blood are mixed with 6 ml of buffer, centrifuged at 800×g for 10 minutes, and the placed on the CellPrep system.

2) After the instrument aspirates the supernatant, the instrument adds the ferrofluids.
3) The instrument performs the incubation and subsequent magnetic separation step.
4) Unbound cells and the remaining plasma are aspirated.
5) Staining reagents are added in conjunction with the permeabilization buffer for fluorescence staining.
6) After incubation by the system, the cells are again separated magnetically and resuspended in the MagNest Cell Presentation Device for analysis using the CellSpotter Analyzer.
7) The Device is placed on the CellSpotter Analyzer, a four-color semi-automated fluorescence microscope.
8) Images are captured that meet the Veridex defined criteria and are shown via a web-based browser for final manual selection.
9) Results of cell enumeration are expressed as the number of cells per 7.5 ml of blood.

Veridex system—CTC enrichment followed by an activation assay:
1) 7.5 ml of blood are mixed with 6 ml of buffer, centrifuged at 800×g for 10 minutes, and then placed on the CellPrep system.
2) After the instrument aspirates the supernatant, the instrument adds the ferrofluids.
3) The instrument performs the incubation and subsequent magnetic separation step.
4) Unbound cells and the remaining plasma are aspirated.
5) The sample is resuspended in 100 μl of stimulation buffer.

Veridex system—CEC and CEPC enrichment followed by an activation assay:
1) Veridex offers a CellTracks Endothelial Cell Kit utilizing capture with an anti-CD146 antibody. The CellTracks Endothelial Cell Kit is used in conjunction with Veridex's CellTracks AutoPrep System for blood sample preparation and the CellTracks Analyzer II to count and characterize CECs and CEPCs from whole blood. The protocol is the same as for the CellSearch Epithelial Cell Kit.

Sample preparation:
1) Peripheral blood from human subjects is drawn in the CellSave Preservative tube according to manufacturer's instructions. The first 3-5 ml is discarded to avoid contamination with epithelial or endothelial cells released from the punctured vein.

Manual Isolation of CSCs:
Evidence is building that tumors contain a small population of putative cancer stem cells with unique self-renewal and survival mechanisms (see, e.g., Sells, *Crit. Rev. Oncol. Hematol.*, 51:1-28 (2004); Reya et al., *Nature*, 414:105-111 (2001); Dontu et al., *Trends Endocrinol. Metal.*, 15:193-197 (2004); and Dick, *Nature*, 423:231-233 (2003)). Cancer stem cells (CSCs) may exist in a quiescent state for a long time, making them resistant to chemotherapeutic drugs which target dividing cells. This cancer-initiating population can be characterized for activation of self-renewal and survival pathways subject to targeted therapy for selective removal. Isolation procedures of CSCs have been described using adherence culture or magnetic microbeads. In this example, a protocol modified from that described in Cote et al., *Clin. Can. Res.*, 12:5615 (2006) is used.

Immunomagnetic CSC isolation—manual isolation followed by an activation assay:
1) Magnetic beads (Dynal AS; Oslo, Norway) are used. These beads are coated with a monoclonal antibody specific for either the CD34 or CD133 surface antigen.
2) Just prior to use, the pre-coated Dynabeads are washed once in an equal volume of PBS with BSA at 0.01%.
3) $1-10^7$ pre-coated Dynabeads are added to 3 ml of the sample.
4) The mixture is incubated for 60 minutes at 2-8° C. with gentle tilting and rotating.
5) The mixture is divided into 1 ml portions and each tube is placed in the magnetic separator (MPL-1 magnet) for at least 6 minutes.
6) The supernatant is discarded and the bead-bound cells are washed three times by resuspending in PBS with BSA at 0.01% followed by magnetic separation.
7) The sample is resuspended in 100 μl of stimulation buffer.

Sample preparation:
1) Bone marrow specimens are obtained from early breast cancer patients following patient informed consent.
2) Processing the bone marrow aspirates is performed as described in Bauer et al., *Clin. Can. Res.*, 6:3552-3559 (2000)). The mononuclear cell fraction containing any disseminated tumor cells is enriched by Ficoll-Hypaque density gradient centrifugation using a Beckman GS-6 centrifuge at 4000×g for 35 minutes and washed twice with PBS.

Cell Stimulation and Lysis of Isolated CTCs:
Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is incubated with Herceptin, Lapatanib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is incubated with Herceptin, Lapatanib, Tarceva, and/or Rapamycin analogs at therapeutically effective concentrations for 30 min. at 37° C.
2) Cells are then stimulated by TGF-α (100 nM), Hrg (10 nM), and/or IGF (100 nM) and incubated at 37° C. for 120 minutes.

Stimulated CTCs are lysed using the following protocol:
1) Fresh lysis buffer is freshly prepared by mixing the reagents set forth in Table 2.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

TABLE 2

| Lysis Buffer recipe (10 ml) | | | |
|---|---|---|---|
| Reagents | Stock conc. | Final conc. | Volume |
| 10% Triton X-100 | 10 | 1 | 1.00 |
| 1M Tris, pH 7.5 | 1 | 0.05 | 0.05 |
| 1M NaF | 1 | 0.05 | 0.05 |
| 5M NaCl | 5 | 0.1 | 0.20 |
| 2M B-glycerolphosphate | 1 | 0.05 | 0.50 |
| 0.1M $Na_3VO_4$ | 0.1 | 0.001 | 0.10 |

TABLE 2-continued

Lysis Buffer recipe (10 ml)

| Reagents | Stock conc. | Final conc. | Volume |
|---|---|---|---|
| 1 mg/ml pepstatin | 1 | 0.10 | |
| Complete mini protease | | | 1 tablet |
| 0.5M EDTA | 0.5 | 0.005 | 0.10 |
| | | Total (ml) | 3.00 |
| | | Water (ml) | 7.00 |

Cell Stimulation and Lysis of Isolated CECs and/or CEPCs:

VEGF is thought to promote survival by activating anti-apoptotic pathways in both CEPCs (Larrivee et al., *J. Biol. Chem.*, 278:22006-22013 (2003)) and mature CECs, which have been sloughed off the vessel wall (Solovey et al., *Blood*, 93:3824-3830 (1999)). VEGF may also stimulate the proliferation of CEPCs or mature CECs, although mature CECs seem to have only a limited proliferative capacity compared with CEPCs (Lin et al., *J. Clin. Invest.*, 105:71-77 (2000)). For these reasons, CECs and/or CEPCs are activated by incubation with VEGF family growth factors prior to lysis.

Cell stimulation:
1) The growth factors VEGF, FGF, PDGF, PIGF, and/or Ang, each at 100 nM, are added to the cells and incubated at 37° C. for 5 minutes.

Cell stimulation with drug treatment:
1) Sample is incubated with Avastin, Nexavar, Sutent, and/or Rapamycin analogs at therapeutically effective concentrations for 30 min. at 37° C.
2) Cells are then stimulated by adding factors VEGF, FGF, PDGF, PIGF, and/or Ang, each at 100 nM, and incubated at 37° C. for 5 minutes.

Cell stimulation with drug treatment (feedback loop):
1) Sample is incubated with Avastin, Nexavar, Sutent, and/or Rapamycin analogs at therapeutically effective concentrations for 30 min. at 37° C.
2) Cells are then stimulated by adding VEGF, FGF, PDGF, PIGF, and/or Ang, each at 100 nM, and incubated at 37° C. for 120 minutes.

Isolated CECs and/or CEPC cells are lysed using the following protocol:
1) Fresh lysis buffer is freshly prepared by mixing the reagents set forth in Table 2.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Cell Stimulation and Lysis of Isolated CSCs:

Stimulated cells:
1) Growth factors TGF-α (100 nM), Hrg (100 nM), and/or IGF (100 nM) are added to the cells and incubated at 37° C. for 5 minutes.

Stimulated cells with drug treatment:
1) Sample is incubated with Herceptin, Lapatanib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Stimulated cells with drug treatment (feedback loop):
1) Sample is incubated with Herceptin, Lapatanib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 120 minutes.

Isolated CSC cells are lysed using the following protocol:
1) Fresh lysis buffer is freshly prepared by mixing the reagents set forth in Table 2.
2) After the final wash, cells are re-suspended on ice in 100 μL of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Example 2

Preparation of Tumor Cell Extracts from Tissue, Biopsy, or Primary Cultures This example illustrates methods for isolating, stimulating, and lysing cells from tumor tissue or biopsy specimens. This example also illustrates methods for initiating, stimulating, and lysing primary cultures of tumor cells isolated from tissue, biopsy, or whole blood. Additional methods for isolating and culturing tumor cells from biological specimens for screening chemotherapeutic agents are described, e.g., in U.S. Pat. Nos. 5,728,541; 6,416,967; 6,887,680; 6,900,027; 6,933,129; and 7,112,415; and in U.S. Patent Publication Nos. 20040023375 and 20050202411. The cellular extracts prepared in accordance with this example can be used in the single detection or proximity assays described herein.

Isolation of Tumor Cells from Primary or Metastatic Tissues:

Cell isolation and culture:
1) Approximately 5-100 mg non-necrotic, non-contaminated tumor tissue are harvested surgically and placed into 100 ml bottle containing sterile cell culture media (e.g., RMPI-1640 with 10% FBS and antibiotics).
2) Samples can be stored or shipped at room temperature within 72 hours of extraction.
3) Samples are rinsed three times in cell culture media.
4) The tissue is minced into small pieces with a scalpel and then disaggregated into a cell suspension by passing through a fine wire mesh.
5) Alternatively, minced tissue is treated with a cocktail containing 0.25% Collagenase II and 0.001% DNase diluted in serum-free cell culture media containing antibiotics. Incubation is for 15-20 min with gentle agitation. Enzymes are removed after treatment by washing 3 times with cell culture media.
6) Cell concentration is adjusted to $10^6$/ml and cells are seeded into 6-well plates and allowed to settle overnight. The following day, the cells are trypsinized and re-seeded into microtiter plates for stimulation with ligands and/or inhibition with targeted drugs.

Cell Stimulation and Lysis of Cells from Disaggregated Tumors:

Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is treated with Herceptin, Lapatanib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is treated with Herceptin, Lapatanib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated cells are lysed using the following protocol:
1) Fresh lysis buffer is freshly prepared by mixing the reagents set forth in Table 2 above.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Isolation of Tumor Cells from Biopsy Specimens:
Cell isolation and culture:
1) Core biopsies are extracted surgically (2 cores for 14 gauge needles, 3 cores for 16 gauge needles, and 4 cores for 18 gauge needles, with 1-2 biopsies for vacuum-assisted biopsies) and placed into a 10 ml sterile vial containing cell culture media as for tumor specimens.
2) Samples can be stored or shipped at room temperature within 72 hours of extraction.
3) Cellular material from core biopsies is disaggregated into a cell suspension by passing through a fine wire mesh.
4) Alternatively, biopsies may be treated with a cocktail containing 0.25% Collagenase II and 0.001% DNase diluted in cell culture media containing antibiotics. Incubation is for 15-20 min with gentle agitation. Enzymes are removed after treatment by washing 3 times with cell culture media.
5) Cell concentration is adjusted to $10^6$/ml and cells are seeded into 6-well plates and allowed to settle overnight. The following day, the cells are trypsinized and re-seeded into microtiter plates for stimulation with ligands and/or inhibition with targeted drugs.

Cell Stimulation and Lysis of Cells from Biopsies:
Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is treated with Herceptin, Lapatanib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is treated with Herceptin, Lapatanib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated cells are lysed using the following protocol:
1) Fresh lysis buffer is freshly prepared by mixing the reagents set forth in Table 2 above.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Initiation of Primary Cultures from Tumor Cells Isolated from Tissue, Biopsy, or Whole Blood:
Cell culture:
1) Tumor cells isolated from tissue, biopsy, or whole blood as described above are cultured in small sterile flasks (e.g., T-25), Petri dishes (e.g., 10 mm), or plates (e.g., 24-well plates) depending on the number of isolated tumor cells.
2) Incubation is done in cell culture media (e.g., RMPI-1640 with 2% FBS and antibiotics) in a humidified 37° C. incubation supplemented with 5% $CO_2$. Over time, cells form a monolayer on the bottom of the vessel and begin to divide. When the cells are close to confluence, they are trypsinized and re-seeded into microtiter plates for stimulation with ligands and/or inhibition with targeted drugs.

Cell Stimulation and Lysis of Primary Cultures from Tumor Cells Isolated from Tissue, Biopsy, or Whole Blood:
Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is treated with Herceptin, Lapatanib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is treated with Herceptin, Lapatanib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated cells are lysed using the following protocol:
1) Fresh lysis buffer is freshly prepared by mixing the reagents set forth in Table 2 above.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Example 3

Single Detection Microarray ELISA with Tyramide Signal Amplification

This example illustrates a multiplex, high-throughput, single detection microarray ELISA having superior dynamic range that is suitable for analyzing the activation states of signal transduction molecules in rare circulating cells:
1) Capture antibody was printed on a 16-pad FAST slide (Whatman Inc.; Florham Park, N.J.) with a 2-fold serial dilution.
2) After drying overnight, the slide was blocked with Whatman blocking buffer.
3) 80 μl of cell lysate was added onto each pad with a 10-fold serial dilution. The slide was incubated for two hours at room temperature.

4) After six washes with TBS-Tween, 80 l of biotin-labeled detection antibody (e.g., a monoclonal antibody recognizing pEGFR or a monoclonal antibody recognizing EGFR regardless of activation state) was incubated for two hours at room temperature.
5) After six washes, streptavidin-labeled horseradish peroxidase (SA-HRP) was added and incubated for 1 hour to allow the SA-HRP to bind to the biotin-labeled detection antibody.
6) For signal amplification, 80 µl of biotin-tyramide at 5 µg/ml was added and reacted for 15 minutes. The slide was washed six times with TBS-Tween, twice with 20% DMSO/TBS-Tween, and once with TBS.
7) 80 µl of SA-Alexa 555 was added and incubated for 30 minutes. The slide was then washed twice, dried for 5 minutes, and scanned on a microarray scanner (Perkin-Elmer, Inc.; Waltham, Mass.).

Example 4

Proximity Dual Detection Microarray ELISA with Tyramide Signal Amplification

This example illustrates a multiplex, high-throughput, proximity dual detection microarray ELISA having superior dynamic range that is suitable for analyzing the activation states of signal transduction molecules in rare circulating cells:
1) Capture antibody was printed on a 16-pad FAST slide (Whatman Inc.) with a serial dilution of from 1 mg/ml to 0.004 mg/ml.
2) After drying overnight, the slide was blocked with Whatman blocking buffer.
3) 80 µl of A431 cell lysate was added onto each pad with a 10-fold serial dilution. The slide was incubated for two hours at room temperature.
4) After six washes with TBS-Tween, 80 µl of detection antibodies for the proximity assay diluted in TBS-Tween/2% BSA/1% FBS was added to the slides. The detection antibodies used were: (1) an anti-EGFR monoclonal antibody that was directly conjugated to glucose oxidase (GO); and (2) a monoclonal antibody recognizing phosphorylated EGFR that was directly conjugated to horseradish peroxidase (HRP). The incubation was for 2 hours at room temperature.
5) Alternatively, the detection step utilized a biotin-conjugate of the monoclonal antibody recognizing phosphorylated EGFR. In these instances, after six washes an additional sequential step of incubation with streptavidin-HRP for 1 hour was included.
6) Alternatively, the detection step utilized an oligonucleotide-mediated glucose oxidase (GO) conjugate of the anti-EGFR antibody. Either the directly conjugated or the biotin-steptavidin (SA) linked conjugate of HRP to the phosphorylated EGFR antibody was used.
6) For signal amplification, 80 µl of biotin-tyramide at 5 µg/ml was added and reacted for 15 min. The slide was washed six times with TBS-Tween, twice with 20% DMSO/TBS-Tween, and once with TBS.
7) 80 µl of SA-Alexa 555 was added and incubated for 30 min. The slide was then washed twice, dried for 5 minutes, and scanned on a microarray scanner (Perkin-Elmer, Inc.).

Example 5

Generation of Activation Profiles for Drug Selection

Figure 2:
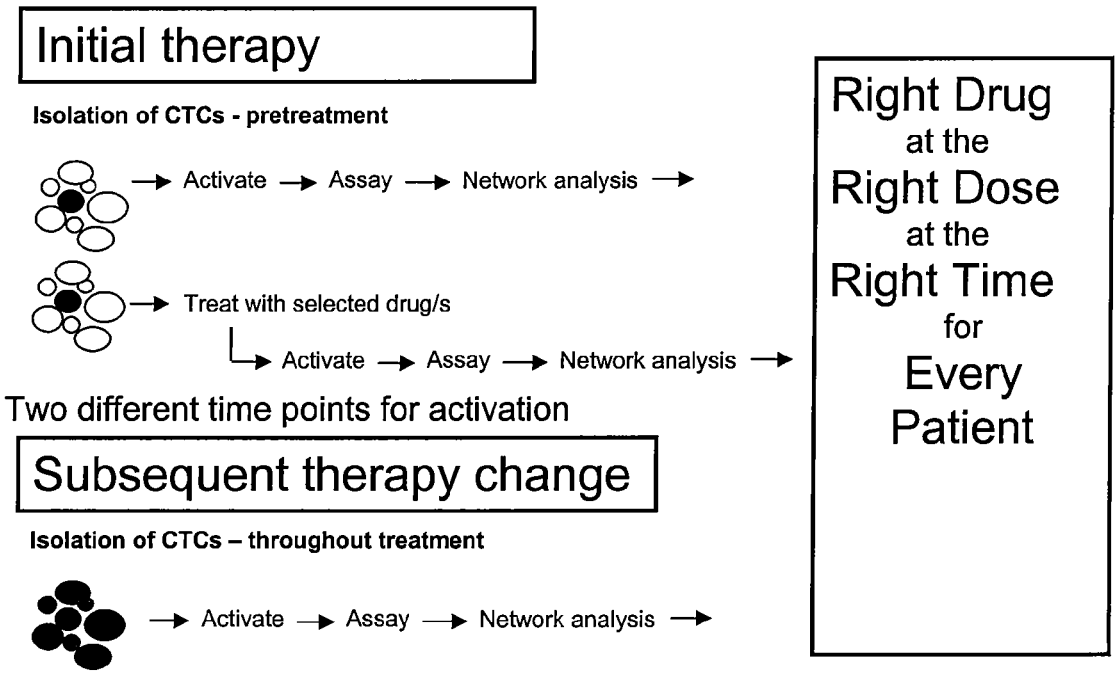
FIG. 2 shows schematically the application of the addressable arrays of the invention for drug selection throughout the course of cancer treatment.

The methods and compositions of the present invention can be applied for drug selection for cancer treatment. A typical protocol entails the generation of two profiles, a reference activation profile and a test activation profile, which are then compared to determine the efficacy of a particular drug treatment regimen (see, FIG. 2).

Reference Activation Profile

To derive a reference activation profile, a blood sample is obtained from a patient having a specific type of cancer (e.g., lung tumor) prior to anticancer drug treatment. Rare circulating cells derived from the cancerous tumor are isolated from the blood sample using, e.g., immunomagnetic separation techniques as described in greater detail herein. The isolated circulating cells can be stimulated in vitro with one or more growth factors. The stimulated cells are then lysed to produce a cellular extract. The cellular extract is applied to an addressable array containing a dilution series of a panel of capture antibodies specific for signal transduction molecules whose activation states may be altered in the patient's type of cancer. Single detection or proximity assays are performed using the appropriate detection antibodies (e.g., activation state-independent antibodies and/or activation state-dependent antibodies) to determine the activation state of each signal transduction molecule of interest. The "Pathway Selection" table shown in Table 1 is particularly useful for selecting which activation states to detect based upon the patient's type of cancer. For example, one patient may have a type of cancer that displays the activation states of the EGFR pathway set forth in "Pathway 1" of Table 1. Alternatively, another patient may have another type of cancer that displays the activation states of the EGFR pathway set forth in "Pathway 2" of Table 1. A reference activation profile is thus generated providing the activation states of signal transduction molecules in the patient's cancer in the absence of any anticancer drugs.

Test Activation Profile

To obtain a test activation profile, a second blood sample is obtained from the patient having the specific type of cancer (e.g., lung tumor) either prior to anticancer drug treatment or after administration of an anticancer drug (e.g., at any time throughout the course of cancer treatment). Rare circulating cells derived from the cancerous tumor are isolated from the blood sample. If isolated cells are obtained from a patient who has not received treatment with an anticancer drug, the isolated cells are incubated with anticancer drugs which target one or more of the activated signal transduction molecules determined from the reference activation profile described above. The "Drug Selection" table (Table A) is particularly useful for selecting appropriate anticancer drugs that are either approved or in clinical trials which inhibit specific activated target signal transduction molecules. For example, if it is determined from the reference activation profile that EGFR is activated, then the cells can be incubated with one or more of the drugs listed in column "A" or "B" of Table A. The isolated cells can then be stimulated in vitro with one or more growth factors. The isolated cells are then lysed to produce a cellular extract. The cellular extract is applied to the addressable array and proximity assays are performed to determine the activation state of each signal transduction molecule of interest. A test activation profile for the patient is thus generated providing the activation states of signal transduction molecules in the patient's cancer in the presence of specific anticancer drugs.

Drug Selection

The anticancer drugs are determined to be suitable or unsuitable for treatment of the patient's cancer by comparing the test activation profile to the reference activation profile. For example, if drug treatment causes most or all of the signal transduction molecules to be substantially less activated than in the absence of the drugs, e.g., a change from strong activation without the drugs to weak or very weak activation with the drugs, then the treatment is determined to be suitable for the patient's cancer. In such instances, treatment is either initiated with the suitable anticancer drug in a patient who has not received drug therapy or subsequent treatment is continued with the suitable anticancer drug in a patient already receiving the drug. However, if the drug treatment is deemed unsuitable for treatment of the patient's cancer, different drugs are selected and used to generate a new test activation profile, which is then compared to the reference activation profile. In such instances, treatment is either initiated with a suitable anticancer drug in a patient who has not received drug therapy or subsequent treatment is changed to a suitable anticancer drug in a patient currently receiving the unsuitable drug.

Example 6

Addressable Arrays for Analysis of Activated Receptor Tyrosine Kinases

FIG. 3 illustrates an addressable receptor tyrosine kinase array of the invention. As discussed herein, receptor tyrosine kinases are key components of many signal transduction pathways involved in cell proliferation. For example, the ErbB family of receptor tyrosine kinase has four family members and plays an important role in fundamental cell processes like cell proliferation, differentiation, and survival. This family of receptor tyrosine kinases has been reported to be overexpressed in a number of different cancers and is associated with worse clinical outcome. On growth factor binding, ErbB1 or EGFR, ErbB3 or HER3, and ErbB4 or HER4 homo- and hetero-dimerize to activate a number of different signaling pathways. ErbB2 or HER2 does not bind to a growth factor and is the preferred hetero-dimerization partner for all three family members. ErbB2 can also homo-dimerize when overexpressed and activate signaling pathways. Homo- or hetero-dimerization of ErbB family results in trans phosphorylation. Auto- or trans-phosphorylation relieves the inhibitory conformation of receptor tyrosine kinases, enabling full kinase activation and at the same time creates binding sites for numerous SH2-containing signaling molecules, such as Src, Shc SHP-1, SHEP-1, and PI(3)K. Adapter proteins or signaling proteins like Shc, Grb2, or PI3K are recruited to the phosphorylated receptors. Phosphorylation of the adapter proteins results in activation of the MAPK and AKT pathways. MAPK pathway activation can be evaluated by determining the phosphorylation status of Erk and Rsk, while PI3K pathway activation can be evaluated by determining the phosphorylation status of Akt and p70S6K.

Thus, the addressable ErbB family chip shown in FIG. 3 allows one to not only determine the expression of the four receptor tyrosine kinases, but also their activation status. Both MAPK and PI3K/Akt pathway activation can also be studied on the addressable chip. Another feature of the chip is the presence of internal controls to determine the tumor content and non-specific IgG to determine any non-specific binding.

Example 7

Addressable Arrays for Analysis of Signal Transduction Pathways in Angiogenesis

FIG. 4 illustrates the configuration of an addressable array for determining the activation state of signal transduction components involved in angiogenesis. As described herein, tumor angiogenesis is critical for the growth of many solid tumors. Among the key signal transduction molecules arrayed include members of the VEGFR, FGFR, and TIE family of receptor tyrosine kinases, which are expressed predominantly on endothelial cells. PDGFR is typically expressed on pericytes. The expression and activation status of these receptors is critical in determining the predominant mechanism of angiogenesis in individual tumor specimens. Growth factors like VEGF and PlGF bind to VEGFR-1 and VEGFR-2 and initiate homo- and hetero-dimerization. Dimerization is followed by phosphorylation of these receptors, which in turn is followed by activation of the MAPK and PI3K/Akt signaling pathways. FGFR, TIE, and PDGFR receptors are also activated in a similar manner. Auto- or trans-phosphorylation relieves the inhibitory conformation of receptor tyrosine kinases, enabling full kinase activation and at the same time creates binding sites for numerous SH2-containing signaling molecules, such as Src, Shc, SHP-1, V-cadherin, SHEP-1, and PI3K. Adapter proteins or signaling proteins like Shc, Grb2, or PI3K are recruited to the phosphorylated receptors. Phosphorylation of the adapter proteins results in activation of the MAPK and AKT pathways. MAPK pathway activation can be evaluated by determining the phosphorylation status of Erk and Rsk, while PI3K pathway activation can be evaluated by determining the phosphorylation status of Akt and p70S6K.

Thus, addressable angiogenesis chips, such as those shown in FIG. 4, allow one to not only determine the expression of all the receptor tyrosine kinases in a patient sample, but also their activation status. Both MAPK and PI3K/Akt pathway activation can also be studied on the addressable chip. The chip has internal controls to determine the tumor or tumor associated cell (CEC's, CEP's, pericytes, etc.) content and non-specific IgG to determine any non-specific binding.

Example 8

Selection of Patients for Treatment of Non-Small Cell Lung Cancer

Current treatments of non-small cell lung cancer (NSCLC) entail the use of both chemotherapeutic and anti-angiogenic treatments. As first line treatments, physicians typically employ carboplatin (C) or carboplatin with Taxol® (T) and Avastin® for non-squamous cell patients. Second line drugs include Taxol®, ALIMTA®, and Tarceva® (for non-smokers, women, and Asians). On-going clinical trials are testing the efficacy of various drug combinations including: Avastin®+Tarceva® in non-squamous patients; sorafenib+carboplatin+Taxol® in all NSCLC including squamous cancer; and ZD6474 (ZACTIMA™)+carboplatin+Taxol® in all NSCLC including squamous cancer.

A number of alterations in key signal transduction components have been demonstrated in NSCLC. These include: EGFR mutations that result in activation; activation of other receptor tyrosine kinases such as c-met; EGFR activation with HER2 and 3 activation or HER2 amplification; EGFR activation with PI3K mutation; EGFR activation with PTEN deletion; and EGFR activation with Ras mutation. Various alterations in different components of signal transduction pathways have been targeted by various forms of chemotherapy.

At the same time, the formation of new blood vessels to tumor cells, a process termed angiogenesis, can be targeted. VEGF is an endothelial cell survival factor which is essential for formation of new blood vessels. Accordingly, one approach to the modulation of VEGF-mediated angiogenesis is to use antibodies directed against the VEGF protein itself or VEGFR. Bevacizumab, a recombinant humanized monoclonal antibody to VEGF, acts synergistically with chemotherapy and has been shown to improve survival in patients with colorectal, breast, and lung cancers.

The example shown below in Table 3 illustrates how an analysis of the pathways active in endothelial cells or ECPs can be used to help physicians decide upon an effective course of treatment. In brief, the activation levels of different components of the VEGF pathway in endothelial cells or ECPs can be determined in the presence of absence of different combinations of test therapeutic agents.

TABLE 3

| Receptor | Expression | Activation (Level of Phosphorylation) | Activation plus Avastin | Activation plus C + T + Avastin |
|---|---|---|---|---|
| VEGFR2: | Medium | Strong | Weak | Weak |
| VEGFR1: | Medium | Strong | Weak | Weak |
| Tie 2 | Low | Weak | Weak | Weak |
| V-Cadherin--R2 complex | Weak | Medium | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

The information shown in Table 3 indicates that signal transduction components that show strong activation as indicated by strong phosphorylation levels are diminished to weak levels by treatment with Avastin or C+T+Avastin. Thus, patients with activated VEGFR-2 and VEGFR-1 pathways should be treated with Avastin or C+T+Avastin.

Examples of other therapeutic agents that target angiogenic signal transduction pathways and which may be used to generate test activation profiles are shown below in Table 4.

TABLE 4

Safety and Efficacy of VEGFR Tyrosine Kinase Inhibitors in NSCLC

| Inhibitor | Target | Common Toxicities | Clinical Activity in NSCLC |
|---|---|---|---|
| Vatalanib | VEGFR-1, -2, -3, PDGFR, c-Kit, c-Fms | Fatigue, nausea, vomiting, elevated liver enzymes, hypertension | Not reported |
| AZD2171 | VEGFR-1, -2, -3, PDGFR | Fatigue, diarrhea, hypertension, anorexia, dyspnea | SD |
| Sunitinib Malate | VEGFR-1, -2, -3, PDGFR, c-Kit | Fatigue, rash, hair depigmentation, hair discoloration, hypertension | PR |
| AG013736 | VEGFR-1, -2, -3, PDGFR, c-Kit | Hypertension, hemoptysis, stomatitis, nausea, diarrhea | Tumor cavitation |
| Sorafenib | VEGFR-2, -3, PDGFR, c-Kit, Raf | Diarrhea, elevated liver enzymes, hypertension, fatigue | SD |
| GW786034 | VEGFR-1, -2, -3, PDGFR, c-Kit | Hypertension, pulmonary embolism, nausea, fatigue, hair depigmentation | SD |
| ZD6474 | VEGFR-1, -2, -3, EGFR | Diarrhea, rash, hypertension | PR |
| CP-547632 | VEGFR-2 | Rash and dry mouth | PR |

Table 4 above lists targets for new anti-angiogenic drugs. The present invention allows the intelligent selection of activation markers that will best predict survival. The most appropriate activation markers may vary between different drugs, and can be used as a guide to select between anti-angiogenic monotherapy versus combination therapy.

Example 9

Selection of Patients for Treatment with Other Anti-Angiogenic Drugs

Additional examples of the application of pathway analyses as disclosed by the present invention for the determination of the suitability various drugs shown in Table 4 are presented below.

ZD6474

ZD6474 (ZACTIMA™) is currently in Phase III clinical trials for the treatment of patients for whom EGFR directed treatments have failed. Specifically, this study is being carried out to assess if adding ZD6474 to best supportive care (BSC) is more effective than best supportive care alone, for the treatment of patients with non-small cell lung cancer, whose disease has recurred after previous chemotherapy and an EGFR tyrosine kinase inhibitor (TKI). ZD6474 is an anticancer drug that targets the growth of new blood vessels to a tumor and thereby might slow the rate at which the tumor may grow. Early studies indicate that ZD6474 has a positive effect on the time that a tumor may take to progress to a further stage. For third line treatment, ZD6474 is given to patients who have relapsed on chemotherapy and EGFR TKI. The structure of ZD6474 is different from Tarceva®/Iressa®, thus the expectation is that it will still inhibit the EGFR and anti-angiogenic pathways (e.g., VEGFR-1, -2, and -3).

Accordingly, the following trials are underway:
Efficacy study comparing ZD6474 in combination with pemetrexed and pemetrexed alone;
A comparative trial of ZACTIMA™ in combination with docetaxel and docetaxel alone in non-small cell lung cancer (NSCLC);
Vandetanib, carboplatin, and paclitaxel in treating patients with Stage I, Stage II, or Stage III NSCLC that can be removed by surgery; and
Efficacy trial comparing ZD6474 with erlotinib in NSCLC after failure of at least one prior chemotherapy.

Selection of patients responsive to drug combinations including ZD6474 using the methods and compositions of the present invention, as shown below in Table 5, would not only decrease the number of patients in Phase III clinical trials but would lead to better patient care.

TABLE 5

| | Tumor cells: | | | |
|---|---|---|---|---|
| Receptor | Expression | Activation (Level of Phosphorylation) | Activation plus ZD 6474 | Activation plus Avastin |
| EGFR: | medium | Strong | V. Weak | Strong |
| ErbB2: | Medium | Strong | V. Weak | Strong |
| ErbB3 | Low | Medium | V. Weak | Medium |
| ErbB4 | Low | Weak | V. Weak | Weak |
| Shc | | Strong | V. Weak | Strong |
| PI3K | | Strong | V. Weak | Strong |
| Erk | | Strong | V. Weak | Strong |
| Rsk | | Strong | V. Weak | Strong |
| Akt | | Strong | V. Weak | Strong |
| P70S6K | | Strong | V. Weak | Strong |

TABLE 6

Endothelial cells:

| Receptor | Expression | Activation (Level of Phosphorylation) | Activation plus ZD 6474 | Activation plus Avastin |
|---|---|---|---|---|
| VEGFR2: | Medium | Strong | Weak | Weak |
| VEGFR1: | Medium | Strong | Weak | Weak |
| Tie 2 | Low | Weak | Weak | Weak |
| V-Cadherin--R2 complex | null | Medium | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

The information in Tables 5 and 6 indicates that ZD6474 down-regulates pathways in both endothelial cells as well as tumor cells.

AZD2171

A number of clinical trials with AZD2171, an agent that inhibits PDGFR and VEGFR, are in progress. For example, a combination of AZD2171 and pemetrexed disodium is being tested for the treatment of patients with relapsed non-small cell lung cancer. The rationale for this combination is that pemetrexed disodium may stop the growth of tumor cells by inhibiting enzymes needed for cell division. AZD2171 provides the additional contribution of stopping the growth of tumor cells by blocking blood flow to the tumor. Thus, giving AZD2171 together with pemetrexed disodium may have a synergistic effect in killing more tumor cells.

Another clinical trial has paired bevacizumab (Avastin®) and AZD2171 in treating patients with metastatic or unresectable solid tumor or lymphoma. The rationale for this combination is that monoclonal antibodies, such as bevacizumab, can block cancer growth in multiple ways. Some block the ability of cancer cells to grow and spread. Others find cancer cells and help kill them or carry cancer-killing substances to them. Bevacizumab and AZD2171 may also stop the growth of cancer cells by blocking blood flow to the cancer. Thus, the administration of bevacizumab together with AZD2171 may synergistically kill more cancer cells.

Other clinical trials are examining the combination of gemcitabine and carboplatin with or without AZD2171 as first-line therapy in treating patients with stage IIIB or stage IV non-small cell lung cancer, and paclitaxel and carboplatin with or without AZD2171 in treating patients with stage III or stage IV non-small cell lung cancer.

Selection of patients responsive to drug combinations including AZD2171 using the methods and compositions of the present invention are shown below in Table 7.

TABLE 7

Endothelial cells and Pericytes:

| Receptor | Expression | Activation (Level of Phosphorylation) | Activation plus AZD 2171 | Activation plus Avastin |
|---|---|---|---|---|
| VEGFR2: | Medium | Strong | Weak | Weak |
| VEGFR1: | Medium | Strong | Weak | Medium |
| Tie 2 | Low | Weak | Weak | Weak |
| V-Cadherin--R2 complex | null | Medium | Weak | Weak |
| PDGFRa | Medium | High | Weak | High |
| PDGFRb | Medium | High | Weak | High |
| Shc | | Strong | Weak | Weak |

TABLE 7-continued

Endothelial cells and Pericytes:

| Receptor | Expression | Activation (Level of Phosphorylation) | Activation plus AZD 2171 | Activation plus Avastin |
|---|---|---|---|---|
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Because PDGF is overexpressed in Avastin®-resistant patients, information such as that presented in Table 7 would suggest that AZD2171, which inhibits PDGFR as well as VEGFR, might be agents of choice to treat such tumors.

Sorafenib

A number of clinical trials with sorafenib (BAY 43-9006) are also in progress. For example, the following studies are underway: (1) comparing carboplatin and paclitaxel plus or minus sorafenib in chemo-naive patients with non-small cell lung cancer; (2) randomized controlled trial comparing safety and efficacy of carboplatin and paclitaxel, plus or minus sorafenib, in chemo-naive patients with stage III-IV non-small cell lung cancer; and (3) sorafenib and bevacizumab in treating patients with refractory, metastatic, or unresectable solid tumors.

Selection of patients responsive to drug combinations including sorafenib using the methods and compositions of the present invention are shown below in Table 8.

TABLE 8

Endothelial cells and Pericytes:

| Receptor | Expression | Activation (Level of Phosphorylation) | Activation plus Sorafinib | Activation plus Avastin |
|---|---|---|---|---|
| VEGFR2: | Medium | Strong | Weak | Weak |
| VEGFR1: | Medium | weak | weak | weak |
| Tie 2 | Low | Weak | Weak | Weak |
| V-Cadherin--R2 complex | null | Medium | Weak | Weak |
| PDGFRa | Medium | High | Weak | High |
| PDGFRb | Medium | High | Weak | High |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Because in Avastin®-resistant patients both VEGF and PDGF are overexpressed, the combination of Avastin® and sorafenib might be effective in shutting down both pathways. In addition, sorafenib inhibits Raf and can thus inhibit the MAPK pathway in all cell types.

Example 10

Other Anti-Angiogenic and Anti-Signaling Therapy Combinations

Both vascular endothelial growth factor and epidermal growth factor receptor (EGFR) may contribute to angiogenesis in tumor tissues and share downstream signaling pathways. Therefore, targeting both pathways might, in principle, result in additive or synergistic antitumor effects. A recent Phase I/II study evaluated the combination of bevacizumab with the EGFR small-molecule tyrosine kinase inhibitor (TKI) erlotinib in patients with nonsquamous refractory advanced non-small cell lung cancer (NSCLC). In Phase II studies, it has been demonstrated that bevacizumab in combination with erlotinib appeared to provide benefit independently of EGFR tyrosine kinase mutation status (see, e.g., Herbst et al., *J. Clin. Oncol.*, 23:2544-2555 (2005)). Thus, clearly shutting down both EGFR and VEGFR-2 appears to be beneficial to patients.

Among the clinical trials in progress in this area are: (1) a study comparing bevacizumab therapy with or without erlotinib for first-line treatment of non-small cell lung cancer (ATLAS); a Phase IIIb, multicenter, randomized, placebo-controlled trial to evaluate the safety and efficacy of chemotherapy+bevacizumab followed by bevacizumab+erlotinib versus bevacizumab+erlotinib placebo in subjects with locally advanced or metastatic NSCLC; (2) a study to evaluate the efficacy of bevacizumab in combination with Tarceva® for advanced non-small cell lung cancer; a second line Phase III, multicenter, placebo-controlled, double-blind, randomized study. Approximately 650 patients will be randomized in a 1:1 ratio to one of two treatment arms: Arm 1: Tarceva®+placebo; Arm 2: Tarceva®+bevacizumab; (3) erlotinib and bevacizumab in treating patients with Stage IIIB or Stage IV primary non-small cell lung cancer who have never smoked; (4) bevacizumab and erlotinib followed by cisplatin or carboplatin and gemcitabine in treating patients with newly diagnosed or recurrent Stage IIIB or Stage IV non-small cell lung cancer; (5) combination of RAD001 with carboplatin, paclitaxel and bevacizumab in non-small-cell lung cancer (NSCLC) patients not treated previously with systemic therapy; (6) cetuximab, paclitaxel, carboplatin, and bevacizumab in treating patients with advanced non-small cell lung cancer; (7) pazopanib+lapatanib; (8) imatinib mesylate and bevacizumab after first-line chemotherapy and bevacizumab in treating patients with Stage IIIB or Stage IV non-small cell lung cancer; and (9) a Phase II trial of AMG 706 or bevacizumab in combination with chemo for advanced NSCLC.

Shown below are examples of patient selection for treatment with various drug combinations using the methods and compositions of the present invention.

TABLE 9

Tumor cells:

| Receptor | Expression | Activation (Level of Phosphorylation) | Activation plus Avastin + Tarceva | Activation plus Avastin |
|---|---|---|---|---|
| EGFR: | medium | Strong | V. Weak | Strong |
| ErbB2: | Medium | Strong | V. Weak | Strong |
| ErbB3 | Low | Medium | V. Weak | Medium |
| ErbB4 | Low | Weak | V. Weak | Weak |
| Shc | | Strong | V. Weak | Strong |
| PI3K | | Strong | V. Weak | Strong |
| Erk | | Strong | V. Weak | Strong |
| Rsk | | Strong | V. Weak | Strong |
| Akt | | Strong | V. Weak | Strong |
| P70S6K | | Strong | V. Weak | Strong |

TABLE 10

Endothelial cells:

| Receptor | Expression | Activation (Level of Phosphorylation) | Activation plus Avastin + Tarceva | Activation plus Avastin |
|---|---|---|---|---|
| VEGFR2: | Medium | Strong | Weak | Weak |
| VEGFR1: | Medium | Strong | Weak | Weak |
| Tie 2 | Low | Weak | Weak | Weak |
| V-Cadherin--R2 complex | null | Medium | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

The information in Tables 9 and 10 indicates that the combination of Avastin® and Tarceva® down-regulates pathways in both endothelial cells as well as tumor cells.

TABLE 11

Patient 5001: (EGFR mutation)

| Receptor | Expression | Activation (Level of Phosphorylation) | Activation plus Tarceva | Activation plus Erbitux |
|---|---|---|---|---|
| EGFR: | High | Strong | V. Weak | Weak |
| ErbB2: | Medium | Strong | V. Weak | Weak |
| ErbB3 | Low | Medium | V. Weak | Medium |
| ErbB4 | Low | Weak | V. Weak | Weak |
| Shc | | Strong | V. Weak | Weak |
| PI3K | | Strong | V. Weak | Medium |
| Erk | | Strong | V. Weak | Medium |
| Rsk | | Strong | V. Weak | Medium |
| Akt | | Strong | V. Weak | Medium |
| P70S6K | | Strong | V. Weak | Medium |

The information in Table 11 suggests that Patient 5001 should be treated with Tarceva® as complete inhibition of receptor phosphorylation and downstream effectors was observed upon Tarceva® addition. Erbitux® did not induce the same level of inhibition. The decision to treat with Tarceva® could be based on:
Pathways activated (activation profile based on the addressable chip) in tumor cells;
Pathways activated on stimulation; or
Inhibition of pathway with Tarceva®.

TABLE 12

Patient 5002: (EGFR mutation resistant to Tarceva ®)

| Receptor | Expression | Activation (Level of Phosphorylation) | Activation plus Tarceva | Activation plus EKB 569 |
|---|---|---|---|---|
| EGFR: | High | Strong | Strong | Weak |
| ErbB2: | Medium | Strong | Strong | Weak |
| ErbB3 | Low | Medium | Medium | Weak |
| ErbB4 | Low | Weak | Weak | Weak |
| Shc | | Strong | Strong | Weak |
| PI3K | | Strong | Strong | Weak |
| Erk | | Strong | Strong | Weak |
| Rsk | | Strong | Strong | Weak |
| Akt | | Strong | Strong | Weak |
| P70S6K | | Strong | Strong | Weak |

From the information in Table 12, this patient would be treated with EKB 569 based on the inhibition profile. Alternatively, the patient can be initially treated with Tarceva®, and on relapse, the patient can be treated with EKB 569.

TABLE 13

Patient 5003: (cMet amplification, relapsed on Tarceva ®)

| Receptor | Expression | Activation (Level of Phosphorylation) | Activation plus Tarceva | Activation plus PHB + Tarceva |
|---|---|---|---|---|
| EGFR: | High | Strong | Strong | Weak |
| ErbB2: | Medium | Strong | Strong | Weak |
| ErbB3 | Low | Medium | Medium | Weak |
| ErbB4 | Low | Weak | Weak | Weak |
| cMet | High | Strong | Strong | Weak |
| Shc | | Strong | Strong | Weak |
| PI3K | | Strong | Strong | Weak |
| Erk | | Strong | Strong | Weak |
| Rsk | | Strong | Strong | Weak |
| Akt | | Strong | Strong | Weak |
| P70S6K | | Strong | Strong | Weak |

The activation profile of this patient shows high expression and phosphorylation of cMet. Thus, the patient should be treated with a combination of cMet and EGFR inhibitor.

TABLE 14

Patient 5004: (EGFR activation along with Her 2 and 3 activation. (⅔ dimer) or Her 2 amplification):

| Receptor | Expression | Activation (Level of Phosphorylation) | Activation plus Tarceva | Activation plus Lapatanib |
|---|---|---|---|---|
| EGFR: | Medium | Strong | V. Weak | V. Weak |
| ErbB2: | High or medium | Strong | Strong | Weak |
| ErbB3 | Low | Strong | Strong | Weak |
| ErbB4 | Low | Weak | V. Weak | V. Weak |
| Shc | | Strong | Strong | V. Weak |
| PI3K | | Strong | Strong | V. Weak |
| Erk | | Strong | Medium | V. Weak |
| Rsk | | Strong | Medium | V. Weak |
| Akt | | Strong | Strong | V. Weak |
| P70S6K | | Strong | Strong | V. Weak |

The pathway profile in Table 14 based on Her 3 phosphorylation suggests using a pan-Her inhibitor. The strong inhibition observed with lapatanib strongly suggests that this agent should be the treatment of choice.

TABLE 15

Patient 5005: (EGFR activation plus PI3K mutation or PTEN deletion):

| Receptor | Expression | Activation (Level of Phosphorylation) | Activation plus Tarceva | Activation plus Tarceva + Mek + mTor inhibitor |
|---|---|---|---|---|
| EGFR: | Medium | Strong | V. Weak | V. Weak |
| ErbB2: | Medium | medium | Weak | Weak |
| ErbB3 | Low | weak | Weak | Weak |
| ErbB4 | Low | Weak | V. Weak | V. Weak |
| Shc | | Strong | Weak | V. Weak |
| PI3K | | Strong | Strong | V. Weak |
| Erk | | Strong | Medium | V. Weak |
| Rsk | | Strong | Medium | V. Weak |
| Akt | | Strong | strong | V. Weak |
| P70S6K | | Strong | strong | V. Weak |

TABLE 16

Patient 5006: (EGFR activation plus Ras mutation):

| Receptor | Expression | Activation (Level of Phosphorylation) | Activation plus Tarceva | Activation plus Tarceva + Mek + mTor inhibitor |
|---|---|---|---|---|
| EGFR: | Medium | Strong | V. Weak | V. Weak |
| ErbB2: | Medium | medium | Weak | Weak |
| ErbB3 | Low | weak | Weak | Weak |
| ErbB4 | Low | Weak | V. Weak | V. Weak |
| Shc | | Strong | Weak | V. Weak |
| PI3K | | Strong | Strong | V. Weak |
| Erk | | Strong | Medium | V. Weak |
| Rsk | | Strong | Medium | V. Weak |
| Akt | | Strong | strong | V. Weak |
| P70S6K | | Strong | strong | V. Weak |

The proliferation of the tumor types with the profiles shown in Tables 15 and 16 are not only driven by the ErbB family but also by activation of downstream events (typically due to a Ras or Raf mutant). Thus, the profiling information indicates that such patients should be treated with an EGFR inhibitor along with drugs which inhibit downstream pathways such as the MAPK and PI3K pathways.

TABLE 17

Patient 5007: Use combination of Tarceva ® + Erbitux ® due to slow internalization (traffic issues)

| Receptor | Expression | Activation (Level of Phosphorylation) | Activation plus Tarceva | Activation plus Tarceva + Erbitux |
|---|---|---|---|---|
| EGFR: | Medium | Strong | Medium | V. Weak |
| ErbB2: | Medium | Strong | Medium | Weak |
| ErbB3 | Low | Strong | Medium | Weak |
| ErbB4 | Low | Weak | V. Weak | V. Weak |
| Shc | | Strong | Weak | V. Weak |
| PI3K | | Strong | Strong | V. Weak |
| Erk | | Strong | Medium | V. Weak |
| Rsk | | Strong | Medium | V. Weak |
| Akt | | Strong | strong | V. Weak |
| P70S6K | | Strong | strong | V. Weak |

The information presented in Table 17 above indicates that this patient should be treated with a combination of Tarceva® and Erbitux®.

TABLE 18

Patient 5008: Selection of patients who are responsive to TKI and not to chemotherpy.

| Receptor | Expression | Activation (Level of Phosphorylation) | Activation plus Tarceva | Activation plus Tarceva + Mek + mTor inhibitor |
|---|---|---|---|---|
| EGFR: | Medium | Strong | V. Weak | V. Weak |
| ErbB2: | Medium | medium | Weak | Weak |
| ErbB3 | Low | weak | Weak | Weak |
| ErbB4 | Low | Weak | V. Weak | V. Weak |
| Shc | | Strong | Weak | V. Weak |
| PI3K | | Strong | Strong | V. Weak |
| Erk | | Strong | Medium | V. Weak |
| Rsk | | Strong | Medium | V. Weak |
| Akt | | Strong | strong | V. Weak |
| P70S6K | | Strong | strong | V. Weak |

The information presented in Table 18 above indicates that patients with Ras mutations are not likely to be responsive to chemotherapy. Thus, patients with such profiles may be candidates for treatment with combinations of TKI.

Example 11

Figure 5:
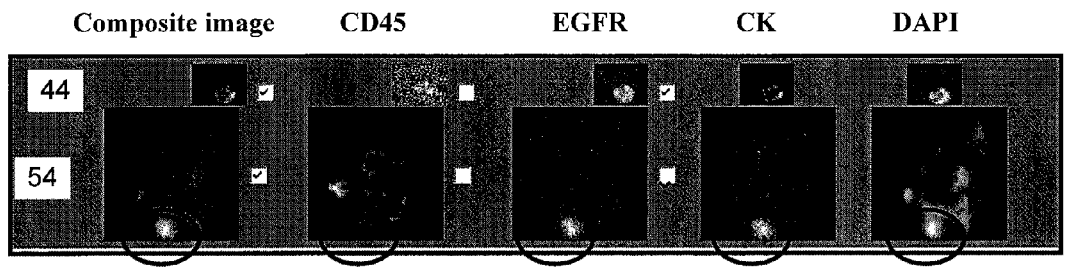
FIG. 5 A-B shows CTC enumeration using the Veridex CellSearch system in patient 2002 (A) and in patient 2015 (B).
Figure 5:
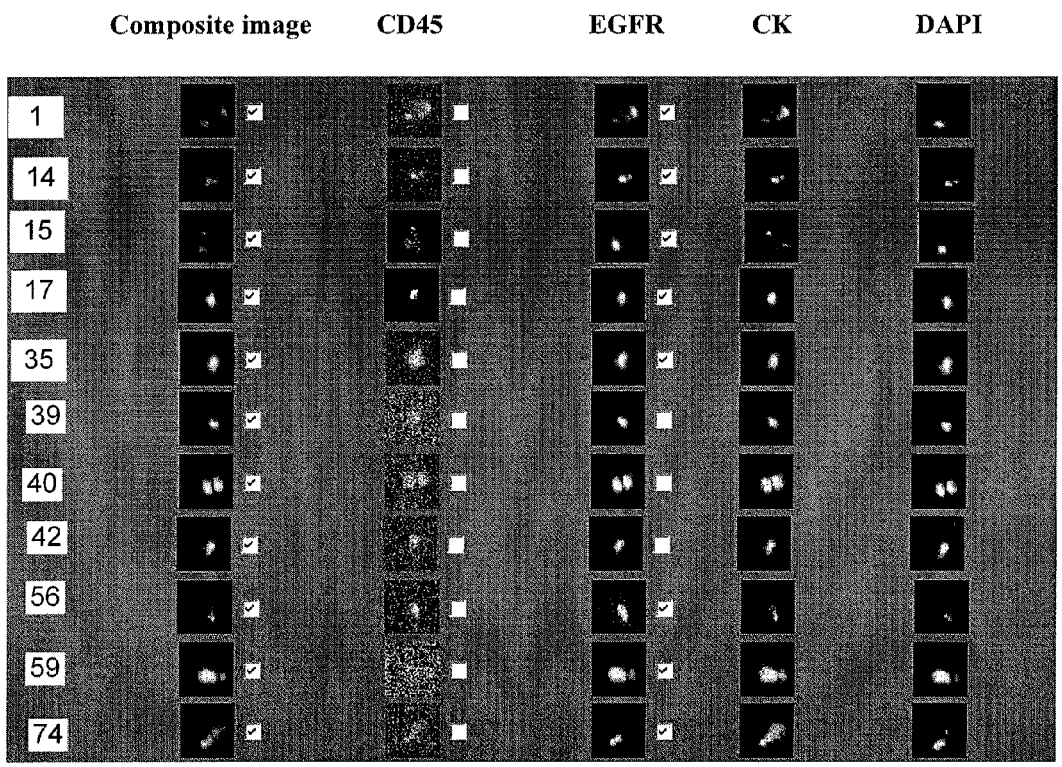

Monitoring Lung Cancer Patients for EGFR and/or HER-2 Activation to Guide Treatment Selection Nine lung cancer patients on therapy were evaluated for CTC number by the Veridex CellSearch™ System, and EGFR and HER-2 phosphorylation using the proximity assays herein. Five of these patients were also tested for EGFR expression on CTCs by staining using the Veridex CellSearch™ Tumor Phenotyping Reagent EGFR. Patient demographics, cancer history, and current medications are given in Tables 19, 20, and 21, respectively. Table 22 shows the numbers of CTCs detected in each sample and the relative phosphorylation levels for EGFR and HER-2. Relative phosphorylation levels were calculated by subtracting the values of normal controls run on the microarrays. FIG. 5 (A and B) shows images, for selected patients, of the CTCs staining for EGFR, cytokeratin (CK) and cytokeratin with DAPI. Cell line controls are SKBr3 and A431 which are positive for EGFR and HER-2 expression, respectively.

Patient 2002 had 2 CTCs detected in the 7.5 mls of blood tested in the CellSearch™ System. Both cells had expression of EGFR and HER-2 detected. This patient was being treated with avastin. Treatment with avastin, either alone or in combination with chemotherapeutics, or chemotherapeutics alone would not have been an adequate therapy for this patient. These data inform the physician that therapy including agents that target both EGFR and HER-2, such as for example, lapatinib, herceptin+zactima, herceptin+erbitux, herceptin+iressa, or herceptin+tarceva, are indicated.

Patient 2015 had 11 CTCs detected in the analysis using the CellSearch™ System. Many of these cells also tested positively for EGFR expression using the Veridex kit. There was significant activation of both EGFR and HER-2. This patient was being treated with avastin, gemzar, and taxotere. Treatment with avastin, either alone or in combination with chemotherapeutics, or chemotherapeutics alone would not have been an adequate therapy for this patient. These data inform the physician that therapy including agents that target both EGFR and HER-2, such as for example, lapatinib, herceptin+zactima, herceptin+erbitux, herceptin+iressa, or herceptin+tarceva, are indicated.

Patients 1023, 2040, 1037, and 1035 had no CTCs in the 7.5 mls of blood tested in the CellSearch™ System. They also tested negatively, as expected, for EGFR and HER-2 phosphorylationin using the proximity assays. The current therapies for these patients is as follows: patient 1023 on carboplatin; patient 2040 on avastin; patient 1037 on avastin, carboplatin, taxol; patient 1035 on avastin, carboplatin, gemzar. Given the lack of CTCs detected in the blood of these patients, continuation of the current therapies is indicated.

Patients 2016 and 1025 each had 3 CTCs in the 7.5 mls of blood tested in the CellSearch™ System. In both cases, there was expression of EGFR on all cells as shown by Veridex EGFR staining. However, neither of these patient samples tested positive for EGFR or HER2 phosphorylation. Systemic therapy had not yet been initiated for these patients. These data inform the physician that the patients' tumor cells are not driven by EGFR/HER-2 pathways, in spite of the fact that there is EGFR expression on the tumor cells. Treating these patients with targeted therapies directed against either EGFR or HER-2 would not be indicated.

Patient 1012 had 3 CTCs in the blood when analyzed in the CellSearch™ System. There was no EGFR staining using the Veridex kit. There was no EGFR or HER2 phosphorylation indicated by the proximity assay analysis. This patient was being treated with avastin, carboplatin, and taxol. Treating this patient with targeted therapies directed against either EGFR or HER-2 would not be indicated.

Table 22 shows a summary of the diagnostic information for each patient and the recommendations for therapy based on data for CTC number and EGFR and HER2 phosphorylation.

TABLE 19

Demographics of the 9 lung cancer patients

| Patient Number | Date of Birth | Gender | Race/Ethnicity |
| --- | --- | --- | --- |
| 02-002 | 19 Apr. 1945 | Male | Caucasian |
| 01-012 | 20 Jun. 1943 | Male | Caucasian |
| 02-015 | 9 Dec. 1950 | Male | Caucasian |
| 02-016 | 5 Mar. 1938 | Female | Caucasian |
| 01-025 | 4 Dec. 1942 | Male | Hispanic/Latino |
| 01-023 | 2 Dec. 1951 | Male | Hispanic/Latino |
| 01-040 | 16 Sep. 1963 | Male | Asian |
| 01-037 | 5 Apr. 1955 | Male | Asian |
| 01-035 | 15 Sep. 1947 | Male | Asian |

TABLE 20

Cancer history of the 9 lung cancer patients

| Patient Number | Cancer Type | Stage | Site of Mets | Date of Diagnosis | Type of Treatment |
| --- | --- | --- | --- | --- | --- |
| 02-002 | LUNG | 4 | ADRENAL | 01 Jul. 2005 | CHEMO |
| 01-012 | LUNG | 4 | BRAIN | 09 Oct. 2007 | RADIATION CHEMOTHERAPY |
| 02-015 | LUNG | 4 | BONE, BRAIN | 24 Oct. 2007 | CHEMO |
| 02-016 | LUNG | 4 | LIVER | 18 Aug. 2007 | CHEMO |
| 01-025 | LUNG | 4 | LIVER | 18 Apr. 2007 | CHEMOTHERAPY |
| 01-023 | LUNG | 4 | LYMPH NODES, BONE | 29 Aug. 2007 | CHEMOTHERAPY |
| 02-040 | LUNG | 4 | BONE, ADRENAL, CEREBELLUM | 06 Dec. 2006 | CHEMO RADIATION |
| 01-037 | LUNG | 4 | RIGHT LOWER LOBE LIVER | 25 Oct. 2007 | CHEMOTHERAPY |
| 01-035 | LUNG | 4 | OTHER LUNG | 22 Dec. 2006 | CHEMOTHERAPY |

TABLE 21

Current medications for the 9 lung cancer patients

| Patient Number | Drug Name | Diagnosis associated with treatment | Dose |
|---|---|---|---|
| 02-002 | AVASTIN | CANCER | 1400 MG QD |
| 01-012 | AVASTIN | CHEMO FOR LUNG CANCER | 1000 MG Q 2 WEEK |
| 01-012 | BENADRYL | PRE-CHEMO | 25 MG Q 2 WEEKS |
| 01-012 | BENAZEPRIL | HYPERTENSION | 20 MG ONE QD |
| 01-012 | BENAZEPRIL HCL | HYPERTENSION | 10 MG ONCE QD |
| 01-012 | CARBOPLATIN | CHEMO FOR LUNG CANCER | 775 MG Q 2 WEEKS |
| 01-012 | DECADRON | PRE-CHEMO | 20 MG Q 2 WEEKS |
| 01-012 | DEXA-METHASONE | PRE-MED FOR CANCER CHEMO | 4 MG ONE TID |
| 01-012 | TAGAMET | PRE-CHEMO | 300 MG Q 2 WEEKS |
| 01-012 | TAXOL | CHEMO FOR LUNG CANCER | 315 MG Q 2 WEEKS |
| 01-012 | ZOFRAN | PRE-CHEMO | 32 MG Q 2 WEEKS |
| 01-012 | ZOLPIDEM | SLEEP AID | 10 MG ONE QD |
| 02-015 | ACTOS | TYPE 2 DIABETES MELLITUS | 30 MG QD |
| 02-015 | AVASTIN | LUNG CA | 1400 MG Q 28 D |
| 02-015 | BENADRYL | RASH | 25 MG Q 28 D |
| 02-015 | COMPAZINE | NAUSEA | 10 MG Q 6-8 HR P |
| 02-015 | DECADRON | NAUSEA | 32 MG EVERY 3 HR |
| 02-015 | DECADRON | NAUSEA | 20 MG Q 28 D |
| 02-015 | DILANTIN | SEIZURES | 800 MG EVERY 3 H |
| 02-015 | DIOVAN | HYPERTENSION | 120 MG BID |
| 02-015 | ENALAPRIL | HYPERTENSION | 80 MG 4XD |
| 02-015 | FLOMAX | PROSTATIC HYPERPLASIA | 8 MG BID |
| 02-015 | GEMZAR | LUNG CA | 2200 MG Q 28 D |
| 02-015 | LIPITOR | HYPER-CHOLESTEROLEMIA | 20 MG BID |
| 02-015 | MAG-OX | HEALTH SUPPLEMENT | BID 800 MG |
| 02-015 | MORPHINE | CANCER PAIN | Q 12 HR 15 MG |
| 02-015 | NEURONTIN | NEUROPATHY | 2400 MG TID |
| 02-015 | TAGAMET | GERD | 300 MG Q 28 D |
| 02-015 | TAXOTERE | LUNG CA | 130 MG Q 28 D |
| 02-015 | VICODIN E.S | PAIN | 750 MG Q 4 HR PR |
| 02-015 | XANAX | ANXIETY | BID 1 MG PRN |
| 02-015 | ZOFRAN | NAUSEA | 32 MG Q 28 D |
| 02-015 | ZOFRAN | NAUSEA | 8 MG Q HR HR |
| 02-015 | ZOMETA | LUNG CA | 4 MG Q 28 D |
| 02-016 | ADVAIR DISKUS | EMPHYSEMA | 500 MG QD |
| 02-016 | FLONASE | SEASONAL ALLERGIES | 100 MCG BID |
| 02-016 | LASIX | HYPERTENSION | 40 MG QD |
| 02-016 | LEVAQUIN | BRONCHITIS | 500 MG QD |
| 02-016 | LEVOXYL | HYPOTHYROID | 0.15 MG QD |
| 02-016 | LIPITOR | HYPER-CHOLESTEROLEMIA | 20 MG QD |
| 02-016 | LISINOPRIL | HYPERTENSION | 10 MG QD |
| 02-016 | LORAZEPAM | INSOMNIA | 3 MG TID |
| 02-016 | NITRO STAT | ANGINA | 0.4 MG PRN |
| 02-016 | NITROGLYCERIN | ANGINA | 5 MG BID |
| 02-016 | PROCRIT | ANEMIA | 40,000 UNITS 5Q |
| 02-016 | VICODIN | CANCER PAIN | 10-325 MG Q- |
| 02-016 | ZANTAC | GERD | 300 MG BID |
| 01-025 | ALLOPURINOL | GERD | 300 MG ONE QD |
| 01-025 | BIAXIN | PROPHYLAXIS | 500 MG ONE PRN |
| 01-025 | HYDRO-CHLOROTHIAZIDE | HYPERTENSION | 50 MG ONE QD |
| 01-025 | IBUPROFEN | PAIN | 800 MG ONE PRN |
| 01-025 | LEVOTHYROXINE | HYPOTHYROIDISM | 0.175 MG ONE QD |
| 01-025 | LISINOPRIL | HYPERTENSION | 40 MG ONE QD |
| 01-025 | LOVASTATIN | HYPER-CHOLESTEROLEMIA | 40 MG ONE QD |
| 01-025 | PAXIL | DEPRESSION | 20 MG ONE QD |
| 01-025 | PROTONIX | GERD | 40 MG ONE QD |
| 01-025 | SPIRIVA | COPD | 18 MCG ONE QHS |
| 01-025 | VERAPAMIL | HYPERTENSION | 240 MG ONE BID |
| 01-023 | BENADRYL | PRE-CHEMO MED | 50 MG Q 3 WEEKS |
| 01-023 | CARBOPLATIN | CHEMOTHERAPY | 500 MG Q 3 WEEKS |
| 01-023 | DECADRON | PRE-CHEMO MED | 20 MG Q 3 WEEKS |
| 01-023 | KYTRIL | PRE-CHEMO MED | 1 MG Q 3 WEEKS |
| 01-023 | NORMAL SALINE | HYDRATION | 250 MG PRN |
| 01-023 | TAGAMET | PRE-CHEMO MED | 300 MG Q 3 WEEKS |
| 02-040 | AVASTIN | LUNG CANCER | 700 MG Q 3 WKS |
| 02-040 | DULCOLOX | CONSTIPATION | 10 MG 1 TAB QD |
| 02-040 | PEPCID | GERD | 10 MG PRN |
| 02-040 | QUINAPRIL | HYPERTENSION | 10 MG QD |
| 02-040 | ZOMETA | LUNG CANCER | 4 MG Q 3 WKS |
| 01-037 | AVASTIN | CHEMOTHERAPY FOR LUNG CANCER | 1200 MG Q 21 DAY |
| 01-037 | BENADRYL | PRE-CHEMOTHERAPY | 50 MG Q 21-DAY |
| 01-037 | BISOPROLOL | HYPERTENSION | 5 MG ONE QD |
| 01-037 | CARBOPLATIN | CHEMOTHERAPY FOR LUNG CANCER | 700 MG Q 21-DA |
| 01-037 | DECADRON | PRE-CHEMOTHERAPY | 20 MG Q 21-DAYS |
| 01-037 | FLUCONAZOLE | FUNGAL | 200 MG TWO QD |
| 01-037 | GLYBURIDE | DIABETES | 2.5 MG ONE QD |
| 01-037 | PROTONIX | ACID REFLUX | 40 MG ONE QD |
| 01-037 | TAGAMET | PRE-CHEMOTHERAPY | 300 MG Q 21-DA |
| 01-037 | TAXOL | CHEMOTHERAPY FOR LUNG CANCER | 340 MG Q 21-DA |
| 01-037 | ZOFRAN | PRE-CHEMOTHERAPY | 32 MG Q 21-DAY |
| 01-035 | AVASTIN | CHEMO FOR LUNG CANCER | 1,000 MG Q 21 DA |
| 01-035 | CARBOPLATIN | CHEMO FOR LUNG CANCER | 700 MG Q 21 DAY |
| 01-035 | DECADRON | PRE-MED FOR CHEMO | 20 MG Q 21 DAY |
| 01-035 | GEMZAR | CHEMO FOR LUNG CANCER | 1,800 MG Q 21 DA |
| 01-035 | MEGACE | APPETITE INCREASE | 20 ML QD |
| 01-035 | ZOFRAN | PRE-MED FOR CHEMO | 32 MG Q 21-DAY |

TABLE 22

Numbers of CTCs (per 7.5 mls), Veridex EGFR staining, and relative EGFR and HER 2 phosphorylation levels for 9 lung cancer samples. Therapy guidance is derived from data.

| Patient ID | Number CTCs | Veridex EGFR staining | Relative pEGFR | Relative pHER2 | Therapy guidance |
|---|---|---|---|---|---|
| 2002 | 2 | + | 1.62 | 1.89 | EGFR/HER 2 inhibitors recommended |
| 1012 | 3 | − | 0.83 | 0.8 | EGFR/HER 2 inhibitors not indicated |
| 2015 | 11 | + | 1.74 | 1.72 | EGFR/HER 2 inhibitors recommended |
| 2016 | 3 | + | 0.61 | 0.65 | EGFR/HER 2 inhibitors not indicated |
| 1025 | 3 | + | 0.94 | 0.69 | EGFR/HER 2 inhibitors not indicated |
| 1023 | 0 | nd | 0.66 | 0.72 | EGFR/HER 2 inhibitors not indicated |
| 2040 | 0 | nd | 1.0 | 1.0 | EGFR/HER 2 inhibitors not indicated |
| 1037 | 0 | nd | 0.93 | 0.64 | EGFR/HER 2 inhibitors not indicated |
| 1035 | 0 | nd | 0.01 | 0.05 | EGFR/HER 2 inhibitors not indicated |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for selecting a suitable anticancer drug for the treatment of a lung tumor, the method comprising:
   (a) lysing cells isolated from the lung tumor after administration of an anticancer drug, or prior to incubation with the anticancer drug, to produce a cellular extract;
   (b) detecting an activation state of one or more analytes in the cellular extract using an assay comprising a plurality of dilution series of capture antibodies specific for the one or more analytes, wherein the activation state is a phosphorylation state, wherein the capture antibodies are restrained on a solid support, wherein the assay comprises:
      (i) incubating the cellular extract with the plurality of dilution series of capture antibodies to form a plurality of captured analytes;
      (ii) washing and then incubating the plurality of captured analytes with detection antibodies comprising a plurality of activation state-independent antibodies and a plurality of activation state-dependent antibodies specific for the corresponding analytes to form a plurality of detectable captured analytes,
      wherein the activation state-independent antibodies are labeled with a facilitating moiety,
      wherein the activation state-dependent antibodies are labeled with a first member of a signal amplification pair, and
      wherein the facilitating moiety, which is glucose oxidase, generates an oxidizing agent which channels to and reacts with the first member of the signal amplification pair, which is a peroxidase in proximity to the glucose oxidase;
      (iii) incubating the plurality of detectable captured analytes with a second member of the signal amplification pair to generate an amplified signal; and
      (iv) detecting the amplified signal generated from the first and second members of the signal amplification pair; and
   (c) determining whether the anticancer drug is suitable or unsuitable for the treatment of the lung tumor by comparing the activation state detected for the one or more analytes with a reference activation profile generated in the absence of the anticancer drug.

2. The method of claim 1, wherein the cells comprise circulating cells of the lung tumor.

3. The method of claim 2, wherein the circulating cells are isolated from a sample by immunomagnetic separation.

4. The method of claim 3, wherein the sample is selected from the group consisting of whole blood, serum, plasma, sputum, bronchial lavage fluid, urine, nipple aspirate, lymph, saliva, fine needle aspirate, and combinations thereof.

5. The method of claim 2, wherein the circulating cells are selected from the group consisting of circulating tumor cells, circulating endothelial cells, circulating endothelial progenitor cells, cancer stem cells, disseminated tumor cells, and combinations thereof.

6. The method of claim 1, wherein the cells are isolated from tumor tissue.

7. The method of claim 1, wherein the isolated cells are stimulated in vitro with growth factors.

8. The method of claim 7, wherein the isolated cells are lysed following growth factor stimulation to produce the cellular extract.

9. The method of claim 1, wherein the anticancer drug comprises an agent that interferes with the function of activated signal transduction pathway components in cancer cells.

10. The method of claim 9, wherein the anticancer drug is selected from the group consisting of a monoclonal antibody, tyrosine kinase inhibitor, chemotherapeutic agent, radiotherapeutic agent, vaccine, and combinations thereof.

11. The method of claim 10, wherein the monoclonal antibody is selected from the group consisting of trastuzumab (Herceptin®), alemtuzumab (Campath®), bevacizumab (Avastin®), cetuximab (Erbitux®), gemtuzumab (Mylotarg®), panitumumab (Vectibix™), rituximab (Rituxan®), tositumomab (BEXXAR®), and combinations thereof.

12. The method of claim 10, wherein the tyrosine kinase inhibitor is selected from the group consisting of gefitinib (Iressa®), sunitinib (Sutent®), erlotinib (Tarceva®), lapatinib (GW-572016), canertinib (CI 1033), semaxinib (SU5416), vatalanib (PTK787/ZK222584), sorafenib (BAY 43-9006), imatinib mesylate (Gleevec®), leflunomide (SU101), vandetanib (ZACTIMA™; ZD6474), and combinations thereof.

13. The method of claim 10, wherein the chemotherapeutic agent is selected from the group consisting of pemetrexed (ALIMTA®), gemcitabine (Gemzar®), sirolimus (rapamycin), rapamycin analogs, platinum compounds, carboplatin, cisplatin, satraplatin, paclitaxel (Taxol®), temsirolimus (CCI-779), everolimus (RAD001), and combinations thereof.

14. The method of claim 10, wherein the radiotherapeutic agent is selected from the group consisting of $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, $^{212}$Bi, and combinations thereof.

15. The method of claim 10, wherein the anticancer drug is a member selected from the group consisting of carboplatin, paclitaxel (Taxol®), bevacizumab (Avastin®), pemetrexed (ALIMTA®), erlotinib (Tarceva®), gemcitabine (Gemzar®), sorafenib (BAY 43-9006), vandetanib (ZACTIMA™; ZD6474), and combinations thereof.

16. The method of claim 1, wherein the one or more analytes comprise a plurality of signal transduction molecules.

17. The method of claim 16, wherein the plurality of signal transduction molecules is selected from the group consisting of receptor tyrosine kinases, non-receptor tyrosine kinases, tyrosine kinase signaling cascade components, and combinations thereof.

18. The method of claim 16, wherein the plurality of signal transduction molecules is selected from the group consisting of EGFR (ErbB1), Her2 (ErbB2), Her3 (ErbB3), Her4 (ErbB4), Raf, SRC, Mek, NFkB-IkB, mTor, PI3K, VEGF, VEGFR-1, VEGFR-2, VEGFR-3, Eph-a, Eph-b, Eph-c, Eph-d, cMet, FGFR, PDGFR, cKit, Flt-3, Tie-1, Tie-2, Flt-3, cFMS, PDGFR, Abl, FTL 3, RET, Kit, HGFR, FGFR1, FGFR2, FGFR3, FGFR4, IGF-1R, and combinations thereof.

19. The method of claim 16, wherein the plurality of signal transduction molecules is selected from the group consisting of ErbB1, ErbB2, ErbB4, and combinations thereof.

20. The method of claim 16, wherein the plurality of signal transduction molecules is selected from the group consisting of VEGF, VEGFR-1, VEGFR-2, VEGFR-3, Eph-a, Eph-b, Eph-c, Eph-d, and combinations thereof.

21. The method of claim 16, wherein the plurality of signal transduction molecules is selected from the group consisting of ErbB1, ErbB2, VEGFR-2, cMet, FGFR, and combinations thereof.

22. The method of claim 16, wherein the plurality of signal transduction molecules is selected from the group consisting of VEGFR-2, VEGFR-3, Raf, PDGFR, cKit, Flt-3, Tie-1, Tie-2, and combinations thereof.

23. The method of claim 16, wherein the plurality of signal transduction molecules is selected from the group consisting of VEGFR-1, VEGFR-2, VEGFR-3, Flt-3, CFMS, PDGFR, cKit, and combinations thereof.

24. The method of claim 1, wherein the solid support is selected from the group consisting of glass, plastic, chips, pins, filters, beads, paper, membrane, fiber bundles, and combinations thereof.

25. The method of claim 1, wherein the capture antibodies are restrained on the solid support in an addressable array.

26. The method of claim 1, wherein the capture antibodies in each dilution series are serially diluted at least 2-fold.

27. The method of claim 1, wherein the activation state-independent antibodies further comprise a detectable moiety.

28. The method of claim 27, wherein the detectable moiety is a fluorophore.

29. The method of claim 27, wherein the amount of the detectable moiety is correlative to the amount of one or more of the analytes.

30. The method of claim 1, wherein the activation state-independent antibodies are directly labeled with the facilitating moiety.

31. The method of claim 1, wherein the activation state-independent antibodies are labeled with the facilitating moiety via hybridization between an oligonucleotide conjugated to the activation state-independent antibodies and a complementary oligonucleotide conjugated to the facilitating moiety.

32. The method of claim 1, wherein the activation state-dependent antibodies are directly labeled with the first member of the signal amplification pair.

33. The method of claim 1, wherein the activation state-dependent antibodies are labeled with the first member of the signal amplification pair via binding between a first member of a binding pair conjugated to the activation state-dependent antibodies and a second member of the binding pair conjugated to the first member of the signal amplification pair.

34. The method of claim 33, wherein the first member of the binding pair is biotin.

35. The method of claim 33, wherein the second member of the binding pair is streptavidin.

36. The method of claim 1, wherein the oxidizing agent is hydrogen peroxide ($H_2O_2$).

37. The method of claim 1, wherein the peroxidase is horseradish peroxidase (HRP).

38. The method of claim 1, wherein the second member of the signal amplification pair is a tyramide reagent.

39. The method of claim 38, wherein the tyramide reagent is biotin-tyramide.

40. The method of claim 39, wherein the amplified signal is generated by peroxidase oxidization of the biotin-tyramide to produce an activated tyramide.

41. The method of claim 40, wherein the activated tyramide is directly detected.

42. The method of claim 40, wherein the activated tyramide is detected upon the addition of a signal-detecting reagent.

43. The method of claim 42, wherein the signal-detecting reagent is a streptavidin-labeled fluorophore.

44. The method of claim 42, wherein the signal-detecting reagent is a combination of a streptavidin-labeled peroxidase and a chromogenic reagent.

45. The method of claim 44, wherein the chromogenic reagent is 3,3',5,5'-tetramethylbenzidine (TMB).

46. The method of claim 1, wherein the lung tumor is derived from a subject with a non-small cell lung cancer (NSCLC).

47. The method of claim 46, wherein the NSCLC is selected from the group consisting of a squamous cell carcinoma, an adenocarcinoma, a large cell carcinoma, bronchoalveolar carcinoma (BAC), and oat cell carcinoma.

48. The method of claim 1, wherein step (b)(iii) comprises washing the plurality of detectable captured analytes prior to incubation with the second member of the signal amplification pair.

* * * * *